United States Patent
Bauer et al.

(10) Patent No.: US 11,957,914 B2
(45) Date of Patent: Apr. 16, 2024

(54) IMPLANTABLE MEDICAL SYSTEMS, DEVICES AND METHODS FOR DELIVERING ASYMPTOMATIC DIAPHRAGMATIC STIMULATION

(71) Applicant: VisCardia, Inc., Beaverton, OR (US)

(72) Inventors: Peter T. Bauer, Portland, OR (US); Gregg Harris, Glen Allen, VA (US)

(73) Assignee: VisCardia, Inc., Beaverton, OR (US)

( * ) Notice: Subject to any disclaimer, the term of this patent is extended or adjusted under 35 U.S.C. 154(b) by 468 days.

(21) Appl. No.: 17/206,684

(22) Filed: Mar. 19, 2021

(65) Prior Publication Data
US 2021/0299450 A1    Sep. 30, 2021

Related U.S. Application Data

(60) Provisional application No. 63/000,961, filed on Mar. 27, 2020.

(51) Int. Cl.
*A61N 1/368* (2006.01)
*A61N 1/05* (2006.01)
*A61N 1/36* (2006.01)

(52) U.S. Cl.
CPC .......... *A61N 1/3684* (2013.01); *A61N 1/057* (2013.01); *A61N 1/3601* (2013.01); *A61N 1/3611* (2013.01)

(58) Field of Classification Search
None
See application file for complete search history.

(56) References Cited

U.S. PATENT DOCUMENTS

| 4,411,268 A | 10/1983 | Cox |
| 5,098,442 A | 3/1992 | Grandjean |

(Continued)

FOREIGN PATENT DOCUMENTS

| CA | 1256507 A | 6/1989 |
| EP | 1588735 A1 | 10/2005 |

(Continued)

OTHER PUBLICATIONS

Neuman, "Biopotential Electrodes". The Biomedical Engineering Handbook: Second Edition, Boca Rato CRC Press LLC (2000).

(Continued)

*Primary Examiner* — Michael W Kahelin
(74) *Attorney, Agent, or Firm* — LOZA & LOZA, LLP; David S. Sarisky

(57) ABSTRACT

Transcardiac diaphragmatic stimulation includes detecting a cardiac event based on signals sensed through a cardiac event sensor located in or on a region of a heart in proximity to a diaphragm, and delivering an ADS therapy through an ADS therapy mechanism that is located in proximity with the region of the heart, to induce a contraction of the diaphragm without inducing a contraction of the heart. The cardiac event sensor may be located a) on an interior surface of a cardiac wall that abuts the diaphragm, or 2) on an exterior surface of the heart, between a cardiac wall and the diaphragm. The ADS therapy mechanism may be located: a) on an interior surface of a cardiac wall that abuts the diaphragm, 2) on a superior surface of the diaphragm that abuts a cardiac wall, or 3) on an inferior surface of the diaphragm at a region of the diaphragm that abuts the heart.

42 Claims, 17 Drawing Sheets

(56) References Cited

U.S. PATENT DOCUMENTS

| | | |
|---|---|---|
| 5,188,098 A | 2/1993 | Hoffman et al. |
| 5,300,094 A | 4/1994 | Kallok et al. |
| 5,358,519 A | 10/1994 | Grandjean |
| 5,392,780 A | 2/1995 | Ogino et al. |
| 5,632,716 A | 5/1997 | Bui et al. |
| 5,693,000 A | 12/1997 | Crosby et al. |
| 5,758,654 A | 6/1998 | Burton-Krahn et al. |
| 5,814,086 A | 9/1998 | Hirschberg |
| 6,415,183 B1 | 7/2002 | Scheiner et al. |
| 6,588,423 B1 | 7/2003 | Sinderby |
| 6,979,297 B2 | 12/2005 | Andresen et al. |
| 7,039,538 B2 | 5/2006 | Baker, Jr. |
| 7,072,708 B1 | 7/2006 | Andresen et al. |
| 7,074,195 B2 | 7/2006 | Nelson et al. |
| 7,096,060 B2 | 8/2006 | Arand et al. |
| 7,096,064 B2 | 8/2006 | Deno et al. |
| 7,113,820 B2 | 9/2006 | Schlegel et al. |
| 7,171,269 B1 | 1/2007 | Addison et al. |
| 7,174,203 B2 | 2/2007 | Arand et al. |
| 7,225,021 B1 | 5/2007 | Park et al. |
| 7,248,923 B2 | 7/2007 | Maile et al. |
| 7,277,757 B2 | 10/2007 | Casavant et al. |
| 7,302,290 B2 | 11/2007 | Bauer |
| 7,340,302 B1 * | 3/2008 | Falkenberg .......... A61N 1/3611 607/9 |
| 7,357,775 B1 | 4/2008 | Koh |
| 7,424,321 B2 | 9/2008 | Wariar et al. |
| 7,435,221 B1 | 10/2008 | Bharmi et al. |
| 7,437,699 B2 | 10/2008 | Morita et al. |
| 7,467,012 B1 | 12/2008 | Park et al. |
| 7,559,903 B2 | 7/2009 | Moussavi et al. |
| 7,668,589 B2 | 2/2010 | Bauer |
| 7,725,181 B1 | 5/2010 | Bornzin et al. |
| 7,819,814 B2 | 10/2010 | Gavriely et al. |
| 7,979,128 B2 | 7/2011 | Tehrani et al. |
| 7,994,655 B2 | 8/2011 | Bauer et al. |
| 8,065,002 B2 | 11/2011 | Arand et al. |
| 8,105,241 B2 | 1/2012 | Nelson et al. |
| 8,137,283 B2 | 3/2012 | Syeda-Mahmood et al. |
| 8,140,164 B2 | 3/2012 | Tehrani et al. |
| 8,185,190 B2 | 5/2012 | Bauer |
| 8,200,336 B2 | 6/2012 | Tehrani et al. |
| 8,233,987 B2 | 7/2012 | Gelfand et al. |
| 8,244,358 B2 | 8/2012 | Tehrani et al. |
| 8,244,359 B2 | 8/2012 | Gelfand et al. |
| 8,265,759 B2 | 9/2012 | Tehrani et al. |
| 8,348,852 B2 | 1/2013 | Bauer et al. |
| 8,409,108 B2 | 4/2013 | Bauer et al. |
| 8,412,323 B2 | 4/2013 | Bauer |
| 8,433,412 B1 | 4/2013 | Westlund et al. |
| 8,548,588 B1 | 10/2013 | Bauer |
| 8,577,448 B2 | 11/2013 | Bauer et al. |
| 8,706,236 B2 | 4/2014 | Ignagni et al. |
| 8,909,341 B2 | 12/2014 | Gelfand et al. |
| 10,335,592 B2 | 7/2019 | Bauer et al. |
| 10,369,361 B2 | 8/2019 | Bauer et al. |
| 10,493,271 B2 | 12/2019 | Bauer et al. |
| 10,537,735 B2 | 1/2020 | Bauer et al. |
| 2002/0103521 A1 | 8/2002 | Swoyer et al. |
| 2002/0188329 A1 | 12/2002 | Struble |
| 2003/0187337 A1 | 10/2003 | Tarassenko et al. |
| 2003/0195571 A1 | 10/2003 | Burnes et al. |
| 2004/0088015 A1 | 5/2004 | Casavant et al. |
| 2004/0127792 A1 | 7/2004 | Siejko et al. |
| 2004/0230105 A1 | 11/2004 | Geva et al. |
| 2005/0027323 A1 | 2/2005 | Mulligan et al. |
| 2005/0043644 A1 | 2/2005 | Stahmann et al. |
| 2005/0065563 A1 | 3/2005 | Scheiner |
| 2005/0080348 A1 | 4/2005 | Stahmann et al. |
| 2005/0080460 A1 | 4/2005 | Wang et al. |
| 2005/0085865 A1 | 4/2005 | Tehrani |
| 2005/0085866 A1 | 4/2005 | Tehrani |
| 2005/0085869 A1 | 4/2005 | Tehrani et al. |
| 2005/0090870 A1 | 4/2005 | Hine et al. |
| 2005/0222515 A1 | 10/2005 | Polyshchuk et al. |
| 2006/0052831 A1 | 3/2006 | Fukui |
| 2006/0079942 A1 | 4/2006 | Deno et al. |
| 2006/0122661 A1 | 6/2006 | Mandell |
| 2006/0122662 A1 | 6/2006 | Tehrani et al. |
| 2006/0155202 A1 | 7/2006 | Arand et al. |
| 2006/0271108 A1 | 11/2006 | Libbus et al. |
| 2007/0021795 A1 | 1/2007 | Tehrani |
| 2007/0038137 A1 | 2/2007 | Arand et al. |
| 2007/0055151 A1 | 3/2007 | Shertukde et al. |
| 2007/0191725 A1 | 8/2007 | Nelson |
| 2007/0265611 A1 | 11/2007 | Ignani et al. |
| 2008/0021510 A1 | 1/2008 | Mi et al. |
| 2008/0125820 A1 | 5/2008 | Stahmann et al. |
| 2008/0167695 A1 | 7/2008 | Tehrani et al. |
| 2008/0177191 A1 | 7/2008 | Patangay et al. |
| 2008/0188904 A1 | 8/2008 | Tehrani et al. |
| 2008/0215106 A1 | 9/2008 | Lee et al. |
| 2008/0255465 A1 | 10/2008 | Nelson |
| 2008/0287820 A1 | 11/2008 | Ignagni et al. |
| 2008/0288010 A1 | 11/2008 | Tehrani et al. |
| 2008/0288015 A1 | 11/2008 | Tehrani et al. |
| 2009/0024176 A1 | 1/2009 | Yun et al. |
| 2009/0048640 A1 | 2/2009 | Bauer et al. |
| 2009/0112107 A1 | 4/2009 | Nelson et al. |
| 2009/0122108 A1 | 5/2009 | Yoshida et al. |
| 2009/0165559 A1 | 7/2009 | Lec |
| 2009/0192561 A1 | 7/2009 | Bauer |
| 2010/0094148 A1 | 4/2010 | Bauer et al. |
| 2010/0094376 A1 | 4/2010 | Penner |
| 2010/0331903 A1 | 12/2010 | Zhang et al. |
| 2011/0015702 A1 | 1/2011 | Ternes et al. |
| 2011/0230932 A1 | 9/2011 | Tehrani et al. |
| 2011/0288609 A1 | 11/2011 | Tehrani et al. |
| 2012/0290036 A1 * | 11/2012 | Karamanoglu ...... A61B 5/4836 607/42 |
| 2012/0296388 A1 | 11/2012 | Zhang et al. |
| 2013/0030488 A1 | 1/2013 | Cho et al. |
| 2013/0030498 A1 | 1/2013 | Karamanoglu et al. |
| 2013/0289636 A1 | 10/2013 | Karamanoglu et al. |
| 2013/0296973 A1 | 11/2013 | Tehrani et al. |
| 2014/0114371 A1 | 4/2014 | Westlund et al. |
| 2014/0172040 A1 | 6/2014 | Bauer |
| 2016/0022988 A1 | 1/2016 | Thieme |
| 2017/0143973 A1 | 5/2017 | Tehrani |
| 2017/0312507 A1 | 11/2017 | Bauer et al. |
| 2017/0312508 A1 | 11/2017 | Bauer et al. |
| 2017/0312509 A1 | 11/2017 | Bauer et al. |
| 2019/0175908 A1 | 6/2019 | Thakkar et al. |
| 2019/0247656 A1 | 8/2019 | Bauer |
| 2019/0255322 A1 | 8/2019 | Bauer et al. |

FOREIGN PATENT DOCUMENTS

| | | |
|---|---|---|
| JP | 2010537716 A | 12/2010 |
| WO | 2009029172 A1 | 3/2009 |
| WO | 2016033245 A1 | 3/2016 |
| WO | 2017053935 A1 | 3/2017 |

OTHER PUBLICATIONS

PCT/US2021/023147 International Search Report & Written Opinion dated Aug. 31, 2021. (21 pages).

Matuschak et al. "Hemodynamic effects of syncrhonous high-frequency jet ventilation during acute hypovolemia." J. of Applied Physiology vol. 61:1 44-53 (Jul. 1986).

Pinsky et al. "Hemodynamic effects of cardiac cycle-specific increases in intrathoracic pressure." J. of Applied Physiology vol. 60:2, 604-612 (Feb. 1986).

Pang et al. Monitoring respiratory activity in neonates using diaphragmatic electromyograph. Medical and Biological Engineering and Computing, vol. 33, 385390 (1995).

Pinsky et al. "Determinants of cardiac augmentation by elevations in intrathoracic pressure." J. of Applied Physiology vol. 58:4, 1189-1198 (Apr. 1985).

Zuber et al. Detection and hemodynamic significance of cardiac pacemaker-induced phrenic nerve stimulation (Original Paper) doi: 10.1111/j.1751-7133.2010.00157.x (Oct. 2008).

(56) References Cited

OTHER PUBLICATIONS

Beeler et al. "Improvement of cardiac function with device-based diaphragmatic stimulation in chronic heart failure patients: the randomized, open-label, crossover Epiphrenic II pilot trial." Euro. J. of Heart Failure 16, 342-349 (2014).

Pinsky et al. "Augmentation of cardiac function by elevantion of intrathoracic pressure." J. of Applied Physiology, vol. 54:4, 950-955 (Apr. 1983).

Roos et al. "Improved cardiac performance through pacing-induced diaphragmatic stimulation: a novel electrophysiological approach in heart failure management?" EP Europace, vol. 11, Issue 2, 191-199 (Feb. 2009).

* cited by examiner

IMPLANTABLE MEDICAL SYSTEMS, DEVICES AND METHODS FOR DELIVERING ASYMPTOMATIC DIAPHRAGMATIC STIMULATION

CROSS-REFERENCE TO RELATED APPLICATION(S)

This claims the benefit of and priority to U.S. Provisional Patent Application Ser. No. 63/000,961, filed Mar. 27, 2020, for "Implantable Medical Systems, Devices and Methods for Delivering Asymptomatic Diaphragmatic Stimulation," the entire disclosure of which is incorporated herein by reference.

TECHNICAL FIELD

The present disclosure relates generally to systems, devices and methods for affecting cardiac function, and more particularly, to implantable medical systems, devices and methods that deliver asymptomatic diaphragmatic stimulation to thereby affect cardiovascular performance.

BACKGROUND

The diaphragm is a dome shaped skeletal muscle structure separating the thoracic and abdominal cavities. It is the major muscular organ responsible for mechanical respiratory motion by deflecting downwards upon contraction during inspiration. The phrenic nerve innervates the diaphragm and acts as the primary method of nervous excitation to signal contraction. The external and internal intercostal muscles also elevate the ribs increasing the anterior-posterior diameter of the thoracic cavity. During inspiration, the movement of the diaphragm results in expansion and negative pressure within the thoracic cavity as the diaphragm and intercostal muscles increase the size of the thorax. The expanding thorax causes the intrathoracic pressure to decrease below atmospheric pressure and air moves into the lungs. During exhalation, the inspiratory muscles relax, and the elastic recoil of the lung tissues, combined with a rise in intrathoracic pressure, causes air to move out of the lungs.

Changes in intrathoracic pressure from diaphragmatic contraction and thoracic expansion may be transmitted to the intrathoracic structures namely the heart, pericardium, great arteries and veins. Spontaneous inspiration produces a negative pleural pressure affecting cardiovascular performance including atrial filling (preload) and resistance to ventricular emptying (afterload). This affect can be observed in cardiovascular hemodynamic parameters during normal function when diaphragmatic contractions is of sufficient duration, intensity and expansiveness to cause inspiration, and used in clinical practice during Vasalva and Mueller maneuvers where patients forcefully inspire or expire using diaphragmatic muscles against a closed glottis causing a rapid change in thoracic pressures. These maneuvers result in pronounced rapid acute changes to intrathoracic pressure, which changes in turn alter pressure gradients associated with the cardiac chambers and vessels to affect cardiac functions, including cardiac filling and output.

The effects of intrathoracic pressure on cardiac systemic performance are complex. Hiccups, which result from rapid partial diaphragmatic contractions causing rapid decreases to intrathoracic pressure, have been previously used to characterize their effects of cardiac and systemic performance. Studies of both animal and human subjects demonstrated changes to hemodynamic parameters including overall ventricular diastolic and systolic pressures, cardiac output and changes to systemic measures including aortic distention and vascular resistance. These studies also demonstrated that rapid intrathoracic pressure effect changes are highly sensitive to timing relative to the cardiac cycle, with different effects observed if the hiccups occur during ventricular diastolic, systole, or during the diastole-systole transition.

Asymptomatic diaphragmatic stimulation (ADS) therapy is based on the cardiac-cycle gaited stimulation of the diaphragmatic muscle tissue to modulate intrathoracic pressure. Current implementations of ADS therapy are centered around the delivery of diaphragmatic stimulation through an extracardiac lead or device having an ADS therapy mechanism, e.g., electrodes, placed on or adjacent to the diaphragm. Placement of the lead or device is facilitated through either endoscopic (laparoscopy, thoracoscopy) or abdominal/thoracic (laparotomy/thoracotomy) surgery. These current implementations are described, for example, in U.S. Pat. No. 7,994,655, titled "Mechanical, Anatomical Heart-Pumping Assist," and in U.S. Pat. No. 10,315,035, titled "Hemodynamic Performance Enhancement Through Asymptomatic Diaphragm Stimulation," and U.S. Pat. No. 10,335,592, titled "Systems, Devices, and Methods for Improving Hemodynamic Performance Through Asymptomatic Diaphragm Stimulation," and U.S. Pat. No. 10,493,271 titled "Implantable Medical Devices, Systems, and Methods for Selection of Optimal Diaphragmatic Stimulation Parameters to Affect Pressures Within the Intrathoracic Cavity."

SUMMARY

Disclosed herein are methods and devices that provide different platforms or pathways for the delivery of asymptomatic diaphragmatic stimulation (ADS) therapy that initiates asymptomatic diaphragmatic movements through one or more of far-field stimulation of the phrenic nerve, far-field stimulation of the diaphragm muscle, and/or direct stimulation of the diaphragm muscle.

In one configuration, the pathway for ADS therapy is through an ADS therapy mechanism, e.g., electrodes, carried by a transvenous, endocardial lead configured to be implanted in an intracardiac location, e.g., the right atrium, the right ventricle, and/or the coronary sinus in the area of the left ventricular or the left atrium. The energy of the ADS therapy is of sufficient strength to pass through or traverse the cardiac wall to stimulate the phrenic nerve and/or the diaphragm muscle to evoke asymptomatic, transient movement of the diaphragm. The endocardial lead may also include a cardiac rhythm management (CRM) therapy mechanism, e.g., electrodes, that enable the delivery of one or more cardiac therapies, such as bradycardia pacing, anti-tachycardia pacing, cardioversion shocks or defibrillation shocks.

In another configuration, the pathway for ADS therapy is through an ADS therapy mechanism, e.g., electrodes, carried by epicardial lead configured to be implanted at an extracardiac location, e.g., on an exterior surface of the heart in the pericardial space. The energy of the ADS therapy is of sufficient strength to pass through or traverse tissue and membrane surrounding the heart to stimulate the phrenic nerve and/or the diaphragm muscle. The epicardial lead may also include a cardiac rhythm management (CRM) therapy mechanism, e.g., electrodes, that enable the delivery of one or more cardiac therapies, such as bradycardia pacing, anti-tachycardia pacing, cardioversion shocks or defibrillation shocks.

In another configuration, the pathway for ADS therapy is through an ADS therapy mechanism, e.g., electrodes, carried by a transvenous, endocardial lead configured to be implanted in an intracardiac location, e.g., the right ventricle or the right atrium, and partially through a cardiac wall, to place the ADS therapy mechanism into direct contact with the diaphragm. This specially configured endocardial lead is referred to herein as a "transcardiac lead." The energy of the ADS therapy is of sufficient strength to directly stimulate the diaphragm muscle. The transcardiac lead may also include a cardiac rhythm management (CRM) therapy mechanism, e.g., electrodes, positioned on the lead so as to be placed at an intracardiac location that enables the delivery of one or more cardiac therapies, such as bradycardia pacing, anti-tachycardia pacing, cardioversion shocks or defibrillation shocks.

In another configuration, the pathway for ADS therapy is through an ADS therapy mechanism, e.g., electrodes, carried by a leadless device configured to be implanted at an extracardiac location between a wall of the heart and the diaphragm, to place the ADS therapy mechanism into direct or close adjacent contact with the diaphragm. The energy of the ADS therapy is of sufficient energy to directly stimulate the diaphragm muscle. The device may also include a cardiac rhythm management (CRM) therapy mechanism, e.g., electrodes, positioned on the device so as to be placed into direct or close adjacent contact with the heart to enable the delivery of one or more cardiac therapies, such as bradycardia pacing, anti-tachycardia pacing, cardioversion shocks or defibrillation shocks.

BRIEF DESCRIPTION OF THE DRAWINGS

Various aspects of devices and methods for delivering ADS therapy through various platforms or pathways will now be presented in the detailed description by way of example, and not by way of limitation, referring to the accompanying drawings, wherein.

DETAILED DESCRIPTION

Electrical stimulation to the diaphragm induces transient, partial, asymptomatic diaphragmatic contractions, which in turn induces changes in intrathoracic pressures. Appropriately timed and configured diaphragmatic stimulation may improve cardiovascular performance and cardiac function, to thereby manage heart failure. For example, diaphragmatic stimulation synchronized with, or otherwise timed to an occurrence of a cyclic cardiac event, such as ventricular systole may accelerate negative intrathoracic cavity pressure (suction) during left ventricular filling to increase filling volume, and then accelerate positive intrathoracic cavity pressure (compression) to augment systolic contractile forces generated by the left ventricle.

Because the management of heart failure is complex and physicians need to optimize numerous various and interdependent physiologic effects between the heart and vessels, an objective of the therapy disclosed herein is to utilize evoked diaphragmatic contractions to optimize the operating intrathoracic pressure conditions on the heart and vessels for improving the patient's overall condition. These include: the blood volume to one or more chambers of the cardiovascular system within the thoracic cavity, end diastolic pressure (preload) that causes changes to systolic output (starling), that mediates intracardiac blood flow (diastolic coronary perfusion) and operating mechanics (efficiency), or for decreasing the compliance of the vessels responsible for cardiac filling (vena cava and right atrium) or for altering the compliance of cardiac vessels to better match the operational ability of the heart (impedance matching or optimization). These indirect physiologic mechanisms augment the direct physiologic mechanism of mechanically augmenting the mechanical forces of the heart and decreasing the vascular resistance to cardiac output.

Asymptomatic Diaphragmatic Stimulation

Figure 1A:
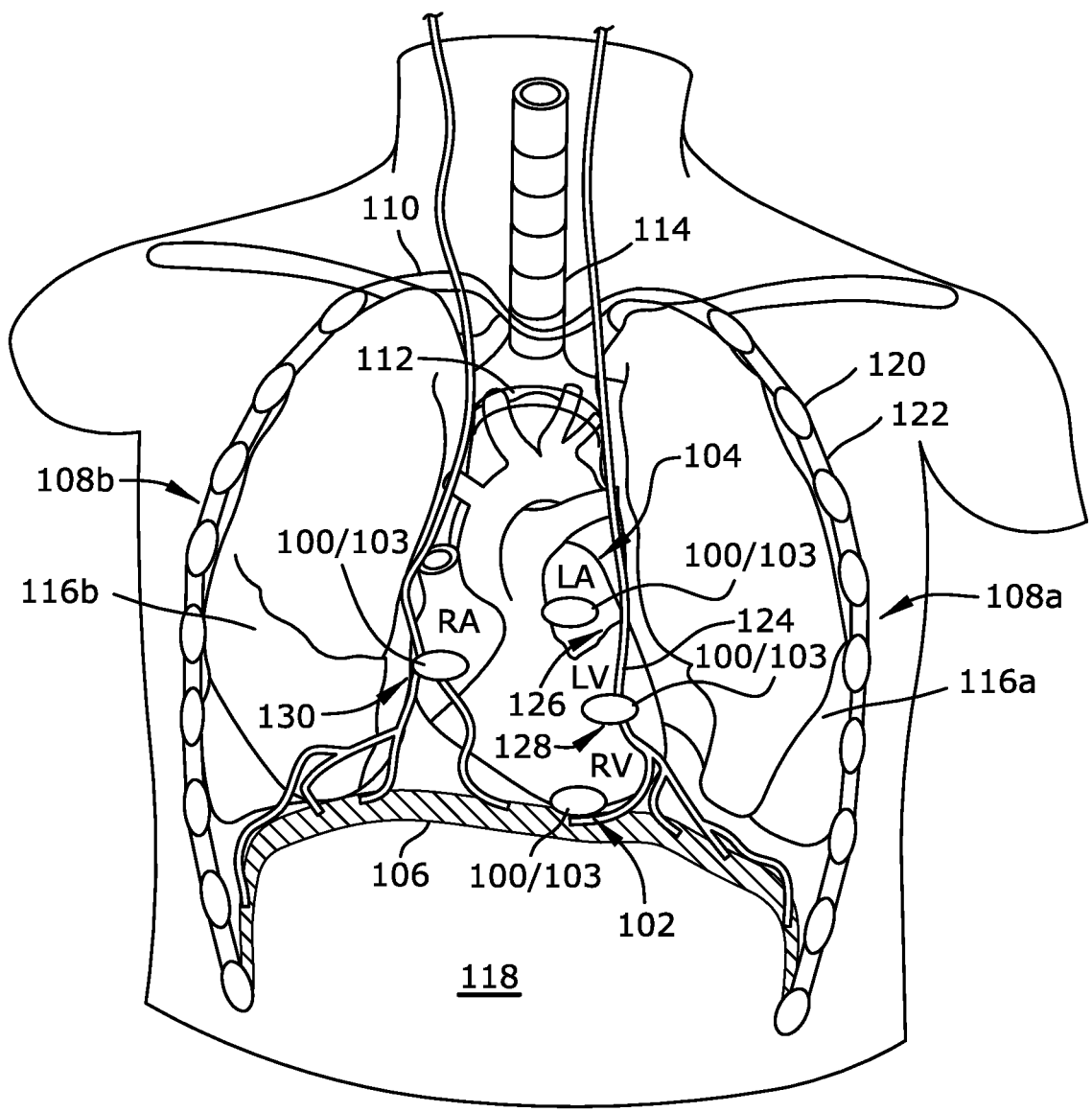
FIG. 1A is a schematic illustration showing various placements of an implantable medical device (IMD) including an asymptomatic diaphragmatic stimulation (ADS) therapy mechanism and a cardiac event sensor, either at intracardiac locations in a heart or extracardiac locations on a surface of the heart, and at interfaces with the diaphragm or the phrenic nerve.

FIG. 1A is a schematic illustration showing various placements of an implantable medical device (IMD) including an asymptomatic diaphragmatic stimulation (ADS) therapy mechanism 100 and a cardiac event sensor 103, either at intracardiac locations in a heart 104 or extracardiac locations on a surface of the heart. In one embodiment, an ADS therapy mechanism 100 and a cardiac event sensor 103 are implanted in or on the right ventricle (RV) of the heart 104 at an interface area 102 of the right ventricle and a diaphragm 106. In another embodiment, an ADS therapy mechanism 100 and a cardiac event sensor 103 are implanted in or on the right atrium (RA) of the heart 104 at an interface area 130 of the right atrium and the diaphragm 106. In another embodiment, an ADS therapy mechanism 100 and a cardiac event sensor 103 are implanted at an interface area 126 of the left atrium (LA) of the heart 104 and the phrenic nerve 124. In another embodiment, an ADS therapy mechanism 100 and a cardiac event sensor 103 are implanted at an interface area 128 of the left ventricle (LV) of the heart 104 and the phrenic nerve 124.

Figure 1B:
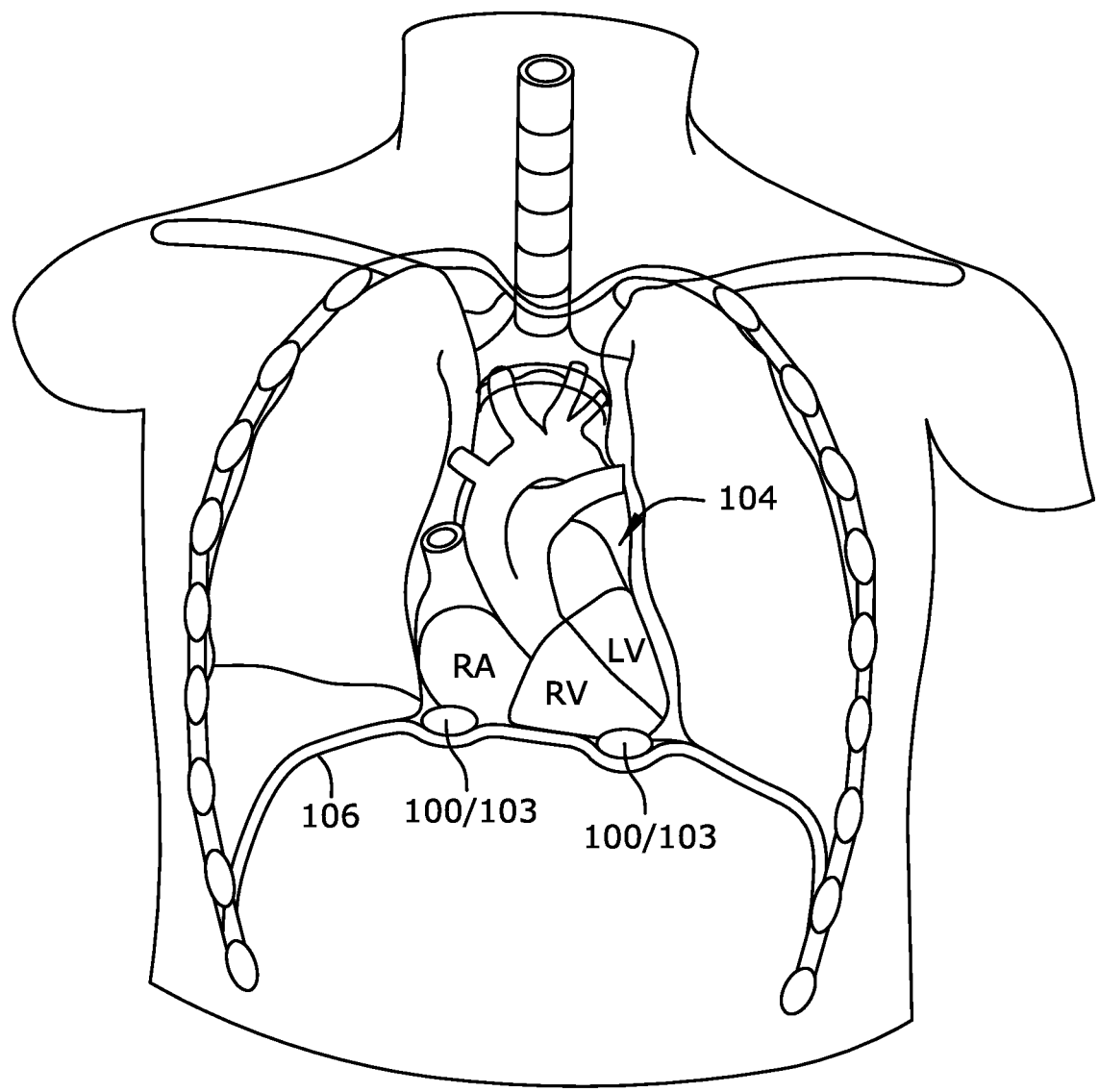
FIG. 1B is a schematic illustration showing various placements of an IMD including an ADS therapy mechanism and a cardiac event sensor at extracardiac locations between the heart and the diaphragm.

FIG. 1B is a schematic illustration showing various placements of an IMD including an ADS therapy mechanism 100 and a cardiac event sensor 103 at extracardiac locations between the heart 104 and the diaphragm 106. It is noted that right atrium (RA) and right ventricle (RV) interface closely to the diaphragm 106. The left ventricle (LV) interfaces to the diaphragm as well, as a portion of it sits behind the right ventricle. In one embodiment, an ADS therapy mechanism 100 and a cardiac event sensor 103 are implanted between the right ventricle (RV) of the heart 104 and a diaphragm 106. In another embodiment, a ADS therapy mechanism 100 and a cardiac event sensor 103 are implanted between the right atrium of the heart 104 and the diaphragm 106.

In each embodiment, the ADS therapy mechanism 100 is configured to deliver stimulation pulses that induce "transient" contractions of the diaphragm 106. The stimulation pulses may be delivered to muscles of the diaphragm 106, to the phrenic nerve 124, or to muscles of the diaphragm and the phrenic nerve in accordance with a diaphragm stimulation program. Stimulation of the muscles of the diaphragm to induce "transient" contractions of the diaphragm and stimulation of the phrenic nerve to induce "transient" contractions of the diaphragm are both referred to herein as "diaphragmatic stimulation." The ADS therapy mechanism 100 may be one or more electrodes configured to be positioned in or on the heart 104, or on or near the diaphragm 106. As used herein, a "transient" contraction of the diaphragm is a short, twitching, caudal followed by cranial motion of the diaphragm that lasts in range of 60 to 180 msec., and is typically about 100 msec. A "partial" contraction of the diaphragm is the part of the diaphragm (less than the entirety of the diaphragm) that exhibits a "transient" contraction.

In each embodiment, the cardiac event sensor 103 is configured to sense cardiac activity that is used by the IMD to detect cardiac events. The sensed cardiac activity may be electrical activity corresponding to cardiac depolarizations, or mechanical activity corresponding to cardiac contractions.

As disclosed herein, each of the ADS therapy mechanism 100 and the cardiac event sensor 103 may be: 1) part of a multi-piece IMD placed partially in or on the heart that delivers diaphragmatic stimulation through a cardiac wall or through tissue or membrane surrounding the heart or through direct contact with the diaphragm, either alone or in combination with delivery of cardiac therapy to the heart, or 2) a single-piece IMD placed between the heart and the diaphragm that delivers diaphragmatic stimulation through direct contact with the diaphragm, either alone or in combination with delivery of cardiac therapy to the heart.

Continuing with FIG. 1A, the thoracic cavity, also referred to as the intrathoracic cavity and the mediastinum, is a hermetically sealed cavity formed by various connected structures. These structures include the diaphragm 106, the thoracic sidewalls 108a, 108b, and upper layered walls 110, 112, near the trachea 114 and the heart 104.

The diaphragm 106 is a dome-shaped skeletal muscle structure located below the lungs 116a, 116b that separates the thoracic cavity from the abdominal cavity 118. The diaphragm 106 defines the lower end of the thoracic cavity and is the major muscular organ responsible for mechanical respiratory motion. The thoracic sidewalls 108a, 108b are formed of ribs 120 and membrane 122 filing the space between the ribs, and define the sidewalls of the thoracic cavity. The upper layered walls 110, 112 are formed of various membranes and vessels which lay over each other to form a seal at the top of the thoracic cavity.

Mechanical respiratory motion includes an inspiration or inhalation phase and an expiration or exhalation phase. As previously mentioned, the diaphragm 106 is the major muscular organ responsible for mechanical respiratory motion. The phrenic nerve 124 innervates the diaphragm 106 and sends signals to the diaphragm to control inspiration and expiration. These signals act as the primary mechanism for initiating contraction of the diaphragm through nervous excitation. Since nervous endings responsible for pain sensation are absent within the diaphragm, a confine of therapy outputs are those which provide the desired hemodynamic effects to the cardiovascular system while simultaneously minimizing the likelihood of field stimulation of pain nerves contained within other nearby innervated thoracic cavity musculature.

Figure 2A:
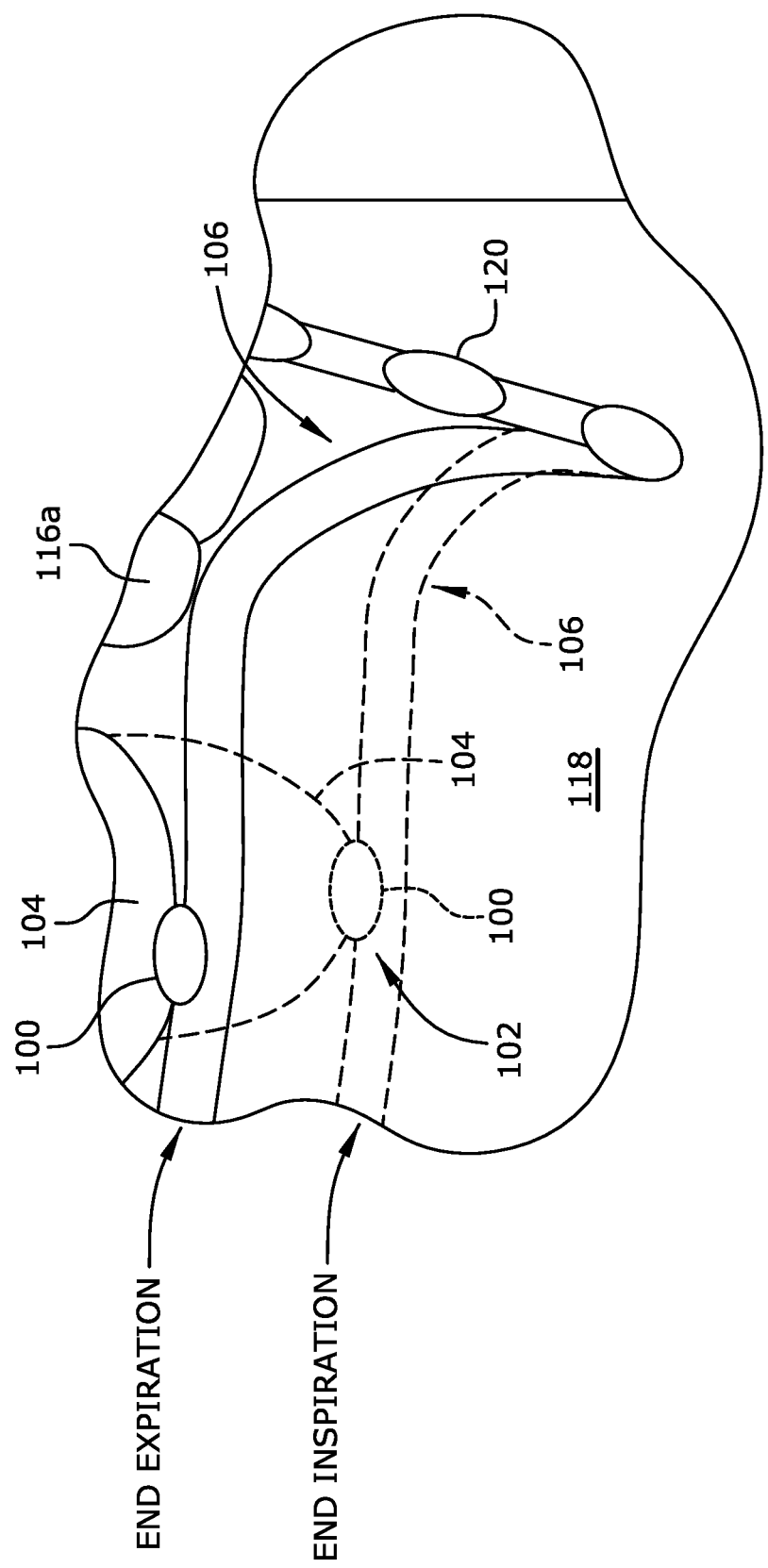
FIG. 2A is an enlarged portion of FIG. 1A illustrating the relative positions of the heart, the diaphragm, and an ADS therapy mechanism located at an interface of the heart and the diaphragm, at each of end expiration and end inspiration.

FIG. 2A is an enlarged portion of the thoracic cavity of FIG. 1A illustrating the relative positions of the heart 104, the diaphragm 106, and an ADS therapy mechanism 100 implanted at an interface area 102 of the right ventricle of a heart 104 and the diaphragm, at each of end expiration (solid lines) and end inspiration (dashed lines). During inspiration, the diaphragm 106 contracts, e.g., flattens out, and deflects downward, in a direction away from the lungs 116a, 116b, while the ribs 120 elevate. The movement of the diaphragm 106 and ribs 120 results in expansion and negative pressure within the thoracic cavity as the diaphragm and intercostal muscles increase the size of the thorax. The expanding thorax causes the pressure within the open space of thoracic cavity, i.e., the intrathoracic pressure, to decrease below atmospheric pressure. The pressure decrease causes external air to move into the lungs 116a, 116b.

During expiration, the diaphragm 106 expands and deflects upward, in the direction of the lungs 116a, 116b. The diaphragm 106, together with the external and internal intercostal muscles around the lungs 116a, 116b relax. The diaphragm 106 expands, e.g., resumes a dome shape, and the ribs 120 de-elevate, thereby reducing the anterior-posterior diameter of the thoracic cavity, and causing the intrathoracic pressure to increase above atmospheric pressure. The increase in intrathoracic pressure in combination with the elastic recoil of lung tissues, causes air to move out of the lungs.

Changes in the pressure within the open space of the thoracic cavity, i.e., the intrathoracic pressure, due to diaphragm contraction and thoracic cavity expansion, and diaphragm expansion and thoracic cavity contraction bring about changes in other pressures within the intrathoracic cavity, including pressures associated with intrathoracic structures like the heart 104, pericardium, great arteries and veins. For example, changes in cardiovascular pressures, such as right atrial (RA) pressure, right ventricular (RV) pressure, left ventricular (LV) pressure, and aortic (AO) pressure result from changes in intrathoracic pressure.

Intrathoracic pressure may be manipulated through controlled delivery of diaphragmatic stimulation through the ADS therapy mechanism 100, to bring about desirable changes in other pressures within the intrathoracic cavity to improve cardiac function. Through delivery of appropriately timed stimulation therapy to the diaphragm 106, transient, asymptomatic, partial contractions of the diaphragm are induced in synchrony or near synchrony with one or more cardiac events to delivery ADS therapy are specified portions of a cardiac cycle. Timing the occurrences of these transient, asymptomatic, partial contractions relative to cardiac events results in changes in intrathoracic pressure, which in turn, increases and/or decreases pressures associated with the heart 104, pericardium, great arteries and veins to thereby improve hemodynamic function of the heart.

Figure 2B:
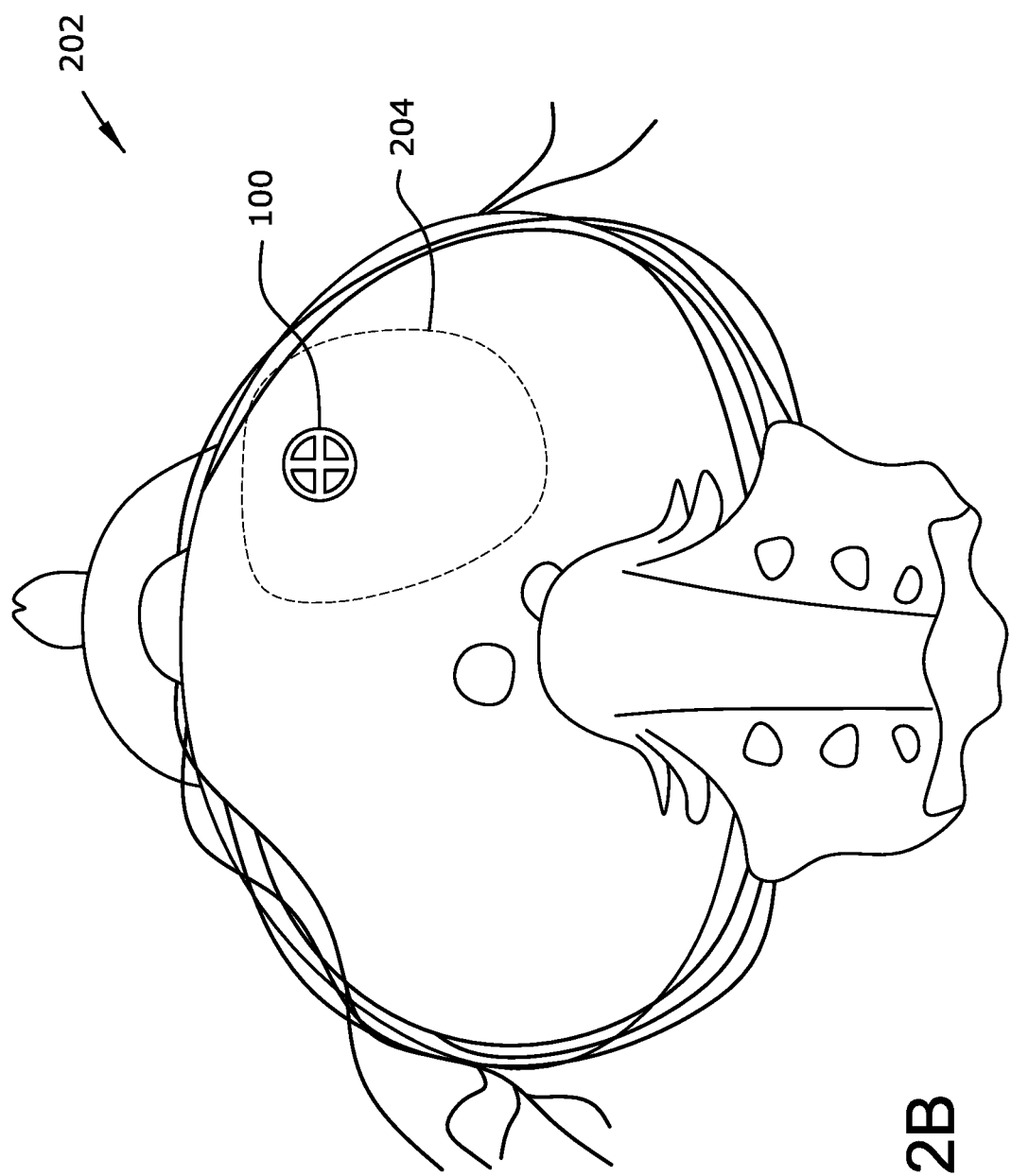
FIG. 2B is an illustration of a diaphragm from the inferior side and marking the location of an ADS therapy mechanism placed on the superior side of the diaphragm at an interface of the heart and the left hemisphere of the diaphragm.

As mentioned above, a "transient" contraction of the diaphragm is a short, twitching, caudal followed by cranial motion of the diaphragm that lasts in range of 60 to 180 msec., and is typically about 100 msec. A "partial" contraction of the diaphragm is the part of the diaphragm (less than the entirety of the diaphragm) that exhibits a "transient" contraction. For example, with reference to FIG. 2B, a diaphragm stimulation pulse delivered through an ADS therapy mechanism 100 placed on the superior side of the diaphragm at an interface between the heart and the left hemisphere 202 of a diaphragm results in contraction of a portion 204 of the left hemisphere that is less than the entirety of the left hemisphere.

Signals indicative of pressures within the intrathoracic cavity, including intrathoracic pressure itself, and other pressures, such as cardiovascular pressures, may be monitored and used as a feedback mechanism to adjust ADS therapy. To this end, one or more parameters that define ADS therapy may be changed to obtain a desired increase and/or decrease in pressures associated with the heart, pericardium, great arteries and veins. For example, in the case of electrical stimulation therapy, one or more of the timing at which an electrical stimulation pulse is delivered, a pulse waveform type, a pulse amplitude, a pulse duration, and a pulse polarity, may be adjusted or changed. See for example, in U.S. Pat. No. 10,315,035, titled "Hemodynamic Performance Enhancement Through Asymptomatic Diaphragm Stimulation," and U.S. Pat. No. 10,335,592, titled "Systems, Devices, and Methods for Improving Hemodynamic Performance Through Asymptomatic Diaphragm Stimulation," and U.S. Pat. No. 10,493,271 titled "Implantable Medical Devices, Systems, and Methods for Selection of Optimal Diaphragmatic Stimulation Parameters to Affect Pressures Within the Intrathoracic Cavity," the disclosures of which are herein incorporated by reference.

Other signals indicative of pressures within the intrathoracic cavity, such as heart sounds, may also be monitored and used as a feedback mechanism to adjust diaphragmatic stimulation therapy. For example, heart sound signals may be used to determine timings between occurrences of cardiac events. One or more parameters that define diaphragmatic stimulation therapy may be changed to obtain a desired increase and/or decrease in these timings.

Devices and Systems for ADS Therapy

As previously described, an ADS therapy mechanism 100 may be: 1) part of a multi-piece IMD placed partially in or on the heart that delivers diaphragmatic stimulation through a cardiac wall or through tissue or membrane surrounding the heart or through direct contact with the diaphragm, either alone or in combination with delivery of cardiac therapy to the heart, or 2) a single-piece IMD placed between the heart and the diaphragm that delivers diaphragmatic stimulation through direct contact with the diaphragm, either alone or in combination with delivery of cardiac therapy to the heart.

Multi-piece IMD

Figure 3A:
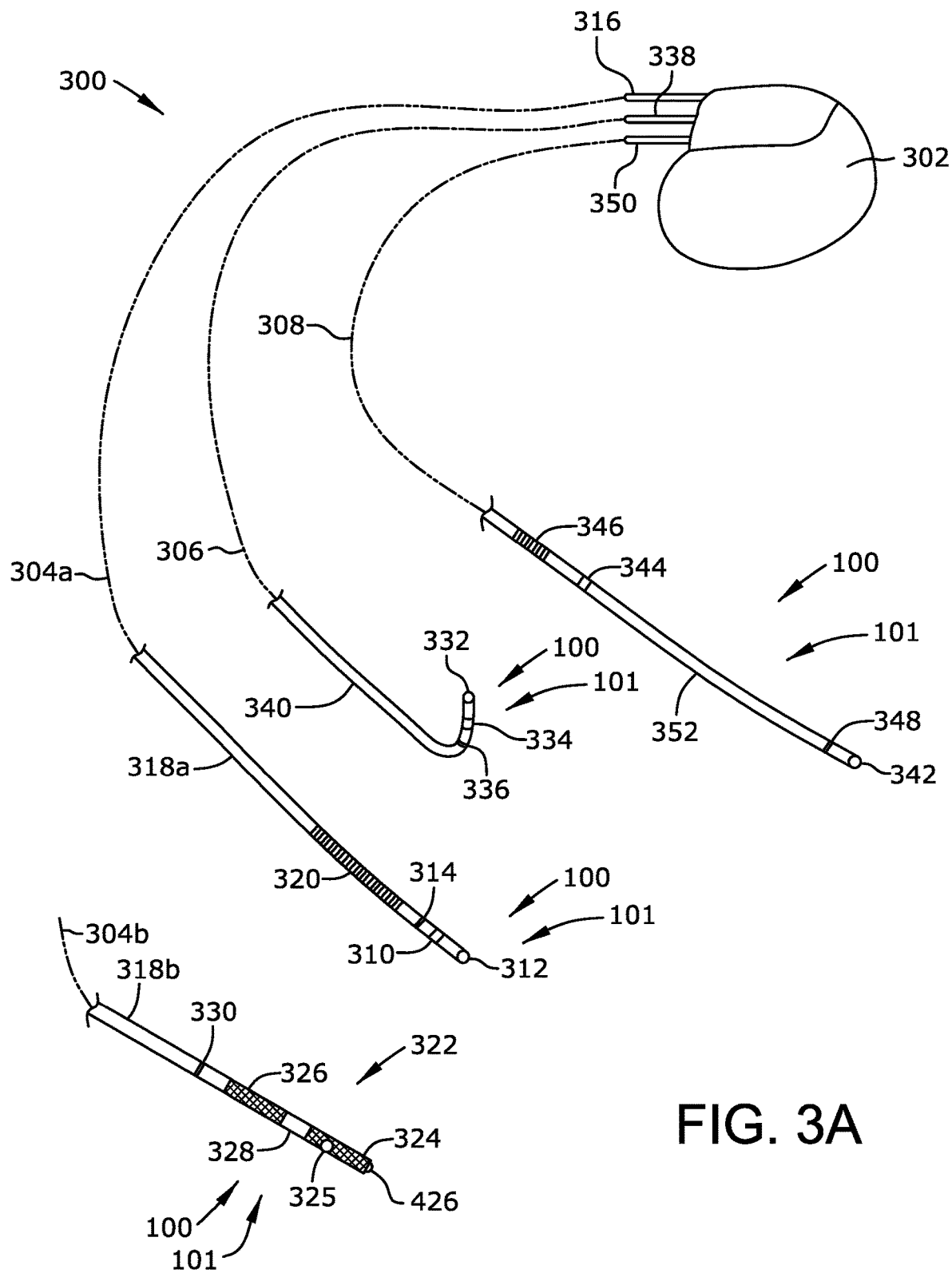
FIG. 3A is an illustration of a multi-piece implantable medical device that includes a can that houses electronics and at least one sub-structure e.g., a transvenous lead, that carries an ADS therapy mechanism.
Figure 3B:
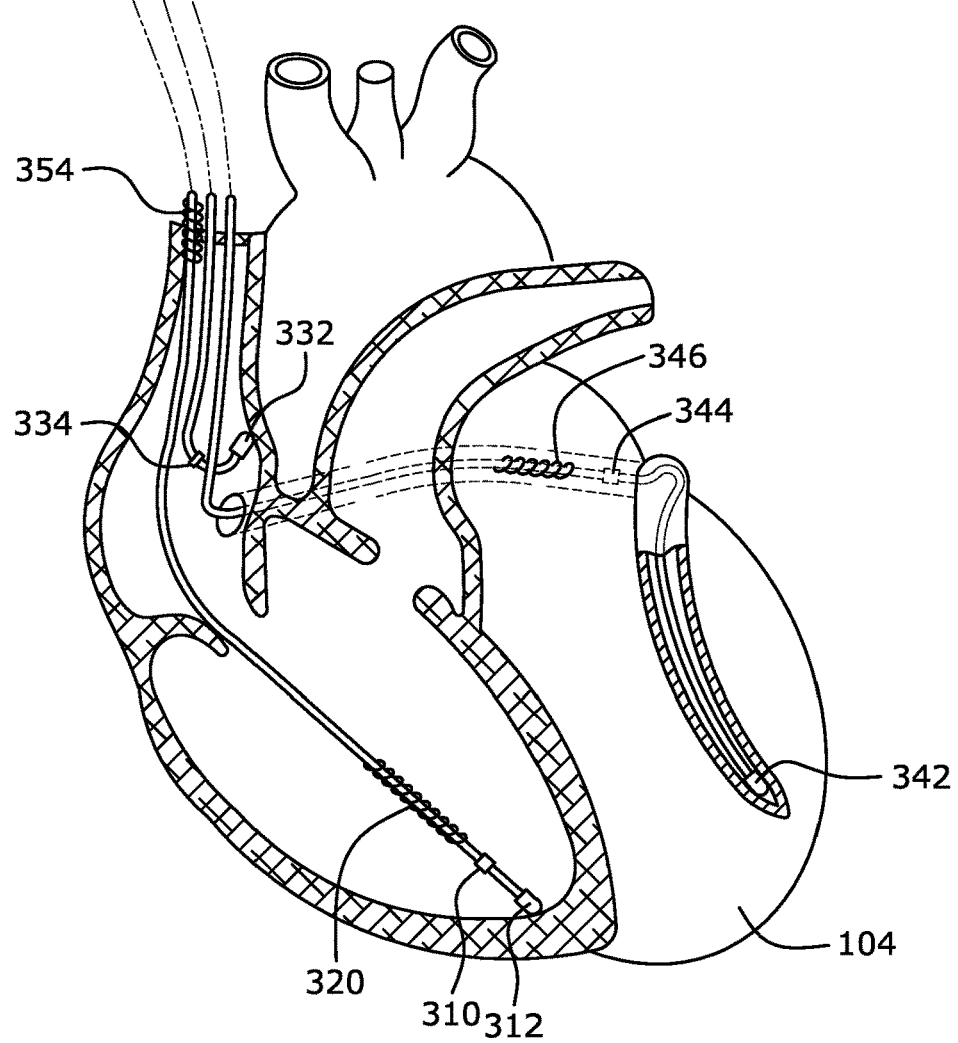
FIG. 3B is an illustration of the transvenous leads of FIG. 3A implanted in a heart.

With reference to FIGS. 3A and 3B, a multi-piece IMD 300 includes a can or housing 302 that houses electronics and at least one sub-structure 304a, 304b, 306, 308, e.g., a lead, that includes an ADS therapy mechanism 100 and a cardiac event sensor 103 at its distal end. The leads 304a, 304b, 306, 308 may also include a CRM therapy mechanism 101. Each of the leads 304a, 304b, 306, 308 is configured to be implanted into the heart through the subclavian vein. The housing 302 may be implanted subcutaneously in a surgically created pocket at an infraclavicular pectoral region in accordance with standard pacemaker implant procedures. Electronics within the housing 302 may be configured to deliver ADS therapy alone, or in combination with cardiac therapy.

In one embodiment, the lead 304a that includes the ADS therapy mechanism 100 and the cardiac event sensor 103 is an endocardial lead configured to be implanted in the right ventricle of a heart. In this embodiment the ADS therapy mechanism 100 includes one or more electrodes 310, 312 that enable the delivery of diaphragmatic stimulation pulses to muscles of the diaphragm. In some configurations, these same electrodes 310, 312 also enable the sensing of electrical activity of the heart, and thereby function as the cardiac event sensor 103. In other configurations, the cardiac event sensor 103 may comprise electrodes different from the electrodes of the ADS therapy mechanism 100.

The ADS therapy mechanism 100 may also include a mechanical transducer 314 that enables the delivery of diaphragmatic mechanical pulses to muscles of the diaphragm. The mechanical transducer 314 may also function to sense mechanical motion/acceleration in order to monitor the lead movement/acceleration and thereby provide a signal which can be used to confirm effectiveness of the ADS therapy. In other words, signals indicative of the lead movement/acceleration may be used to confirm that the delivered ADS therapy captured the diaphragm, i.e., resulted in a partial, transient contraction of the diaphragm. Alternatively, the ADS therapy mechanism may include a separate mechanical transducer, e.g., motion sensor (not shown), that senses mechanical motion/acceleration in order to monitor the lead movement/acceleration. These components, e.g., electrodes, mechanical transducer, motion sensor, are electrically coupled to a connector (not shown) at the proximal end 316 of the lead through wires extending through a lead body 318a.

In cases where the multi-piece IMB 300 is configured to deliver cardiac therapy to the heart, the lead 304a also includes a CRM therapy mechanism 101. The CRM therapy mechanism 101 may include one or more electrodes. In some configurations, the electrodes of the CRM therapy mechanism 101 may be the electrodes 310, 312 of the ADS therapy mechanism 100. In other configurations, the electrodes of the CRM therapy mechanism 101 may be the electrodes of the cardiac event sensor 103. In other configurations, the electrodes of the CRM therapy mechanism 101 may be electrodes different from the electrodes of the ADS therapy mechanism 100 and the electrodes of the cardiac event sensor 103. In any case, the electrodes of the CRM therapy mechanism 101 are configured to deliver cardiac therapies, such as bradycardia pacing, anti-tachycardia pacing. These electrodes may include an additional electrode, such as a RV coil electrode 320 that is configured to deliver cardioversion shocks or defibrillation shocks.

Figure 4:
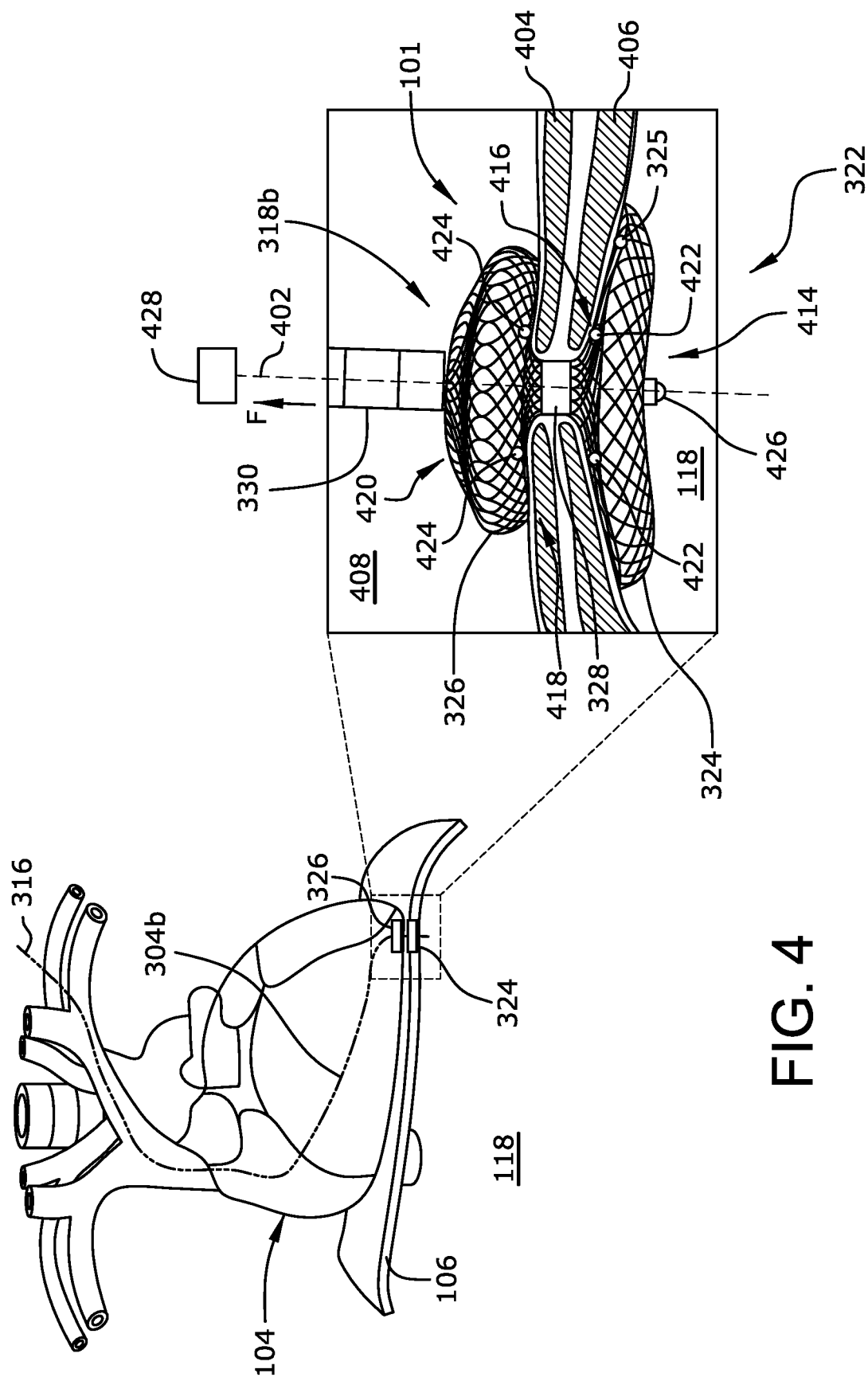
FIG. 4 is an illustration of one of the transvenous leads of FIG. 3A having a distal region implanted through a wall of the heart and into the abdominal cavity to place an ADS therapy mechanism in contact with the diaphragm, and a cardiac rhythm management (CRM) therapy mechanism in contact with the heart.

With additional reference to FIG. 4, in another embodiment, the transcardiac lead 304b that includes the ADS therapy mechanism 100 and the cardiac event sensor 103 is a transcardiac lead configured to be implanted in a chamber of the heart, such as the right ventricle, and at least partially through a cardiac wall of the heart 104, through the diaphragm 106, and into the abdominal cavity. in this embodiment, the transcardiac lead 304b includes a distal end structure 322 having a distal portion 324 and a proximal portion 326 separated by a seal structure 328. The distal portion 324 and a proximal portion 326 are formed of an expandable metal mesh structure that is configured to expand upon application of a pulling force F along the axis 402 of the lead body in the proximal direction.

In their expanded states, the distal portion 324 and a proximal portion 326 assume geometric shapes characterized by a cross-section dimension. For example, the distal portion 324 and a proximal portion 326 may assume a circular, disc shape having a diameter. In some embodiments, such as shown in FIG. 4, the cross-section dimension of the distal portion 324 is greater than the cross-section dimension of the proximal portion 326. The larger cross-section of the distal portion 324 serves to retain the distal end structure 322 in place, post-deployment by providing increased resistance to the upward forces F applied to the lead by a beating heart 104, that may otherwise dislodge the distal end structure 322, e.g., pull the distal portion 324 into the chamber of the heart.

In its expanded state, the distal portion 324 is characterized by a distal, abdominal-cavity facing side 414, and a proximal, diaphragm-facing side 416. Similarly, in its expanded state, the proximal portion 326 is characterized by a distal, cardiac-wall facing side 418, and a proximal, chamber-facing side 420.

The seal structure 328 is configured to: a) ensure electrical insulation between cardiac tissue 404 and diaphragmatic muscle 406 post deployment, and b) ensure that cardiac cavity 408, the thoracic cavity 410, and the abdominal cavity 118 are sealed from each other during and post deployment of the lead. The seal structure 328 may be made out of silicon, and when a pulling force F along the axis 402 of the lead body 318b in the proximal direction is a applied, the seal structure is compressed along the axis of the lead body and thereby flattens and expands radially outward from and generally perpendicular relative to the axis of the lead body.

In this embodiment the ADS therapy mechanism 100 includes one or more distal electrodes associated with the distal portion 324 that enable the delivery of diaphragmatic stimulation pulses to muscles 406 of the diaphragm. In some embodiments, the metal structure forming the distal portion 324 may be electrically conductive, and the one or more distal electrodes may correspond to the entirety of the metal structure forming the distal portion. In some embodiments the one or more distal electrodes may correspond to a part of the metal structure forming the distal portion 324. For example, the metal structure forming the proximal, diaphragm-facing side 416 of the distal portion 324 may be electrically conductive, and the one or more electrodes may correspond to the proximal, diaphragm-facing side. In some embodiments, the one or more distal electrodes may correspond to separate electrodes 422 that are secured to the proximal, diaphragm-facing side 416 of the distal portion 324.

The distal portion 324 may also include a mechanical transducer 325 that enables the delivery of diaphragmatic mechanical pulses to muscles 406 of the diaphragm 106 that induce an asymptomatic, partial, transient contraction of the diaphragm. The mechanical transducer 325 may be located on the diaphragm-facing side 416 of the distal portion 324. The same mechanical transducer 325 may also function to sense mechanical motion/acceleration in order to monitor the movement/acceleration of the transcardiac lead 304b and thereby provide a signal which can be used to confirm capture of the diaphragm 106 during ADS therapy. Alternatively, the ADS therapy mechanism 100 may include a second mechanical transducer, e.g., motion sensor (not shown), that operates separate from the mechanical transducer 325 to sense mechanical motion/acceleration in order to confirm capture of the diaphragm 106 during ADS therapy.

In this embodiment the cardiac event sensor 103 includes one or more proximal electrodes associated with the proximal portion 326 that enable the sensing of electrical activity of the heart through cardiac tissue 404. In some embodiments, the metal structure forming the proximal portion 326 may be electrically conductive, and the one or more proximal electrodes may correspond to the entirety of the metal structure forming the proximal portion. In some embodiments the one or more proximal electrodes may correspond to a part of the metal structure forming the proximal portion 326. For example, the metal structure forming the distal, cardiac-wall facing side 418 of the proximal portion 326 may be electrically conductive, and the one or more electrodes may correspond to the distal, cardiac-wall facing side. The one or more proximal electrodes may correspond to separate electrodes 424 that are secured to the distal, cardiac-wall facing side 418 of the proximal portion 326.

These components, e.g., electrodes 422, 424, mechanical transducer 325, motion sensor (not shown), are electrically coupled to a connector (not shown) at the proximal end 316 of the lead through wires extending through the lead body 318b. The electrical insulation between cardiac tissue 404 and the diaphragmatic muscle 406 provided by the seal structure 328 enables: a) the independent registration of electrical signals sensed from the cardiac muscle by the electrodes of the proximal portion 326 and the electrical signals sensed from the diaphragm by the electrodes of the distal portion 324, and b) the independent delivery of pacing stimulation pulses by the electrodes of the proximal portion 326 to the cardiac muscle and the delivery of diaphragmatic stimulation pulses by the electrodes of the distal portion 324 to the diaphragm.

In cases where the multi-piece IMB 300 is configured to deliver cardiac therapy to the heart, the transcardiac lead 304b also includes a CRM therapy mechanism 101. The CRM therapy mechanism 101 may include one or more electrodes. In some configurations, the electrodes of the CRM therapy mechanism 101 may be the electrodes of the cardiac event sensor 103. In other configurations, the electrodes of the CRM therapy mechanism 101 may be electrodes different from the electrodes of the cardiac event sensor 103. In any case, the electrodes of the CRM therapy mechanism 101 are configured to deliver cardiac therapies, such as bradycardia pacing, anti-tachycardia pacing. These electrodes may include an additional electrode, such as a proximal electrode 330 that is configured to sense cardiac activity and deliver cardiac therapy in conjunction with the one or more proximal electrodes associated with the proximal portion 326 of the distal end structure 322. The one or more proximal electrodes associated with the proximal portion 326 may be configured to deliver cardioversion shocks or defibrillation shocks. For example, a proximal electrode corresponding to the entirety of the metal structure forming the proximal portion 326 of the distal end structure 322 may be used to deliver cardioversion shocks or defibrillation shocks.

Figure 5:
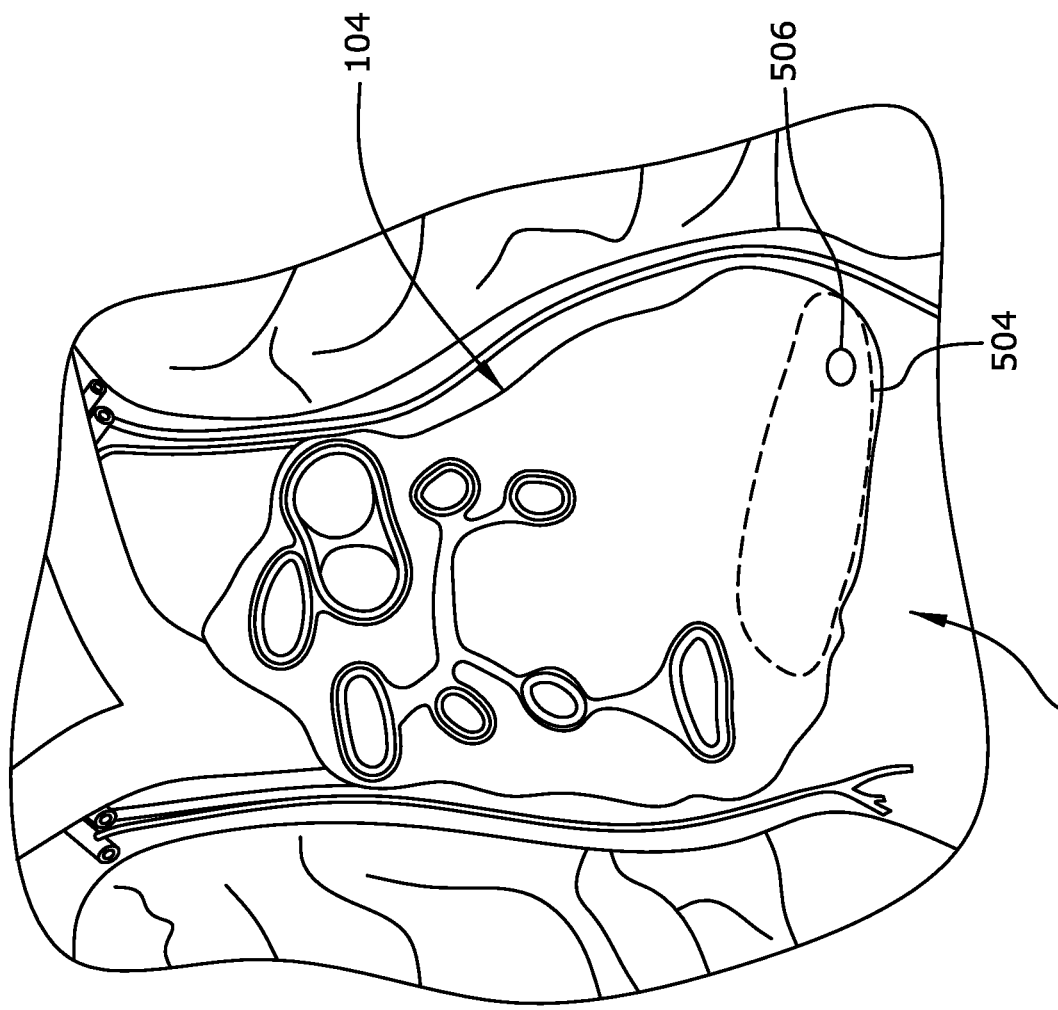
FIG. 5 is an illustration of an implant area for the distal end region of the lead illustrated in FIG. 4.

The transcardiac lead 304b may be configured as an over-the-wire lead, that enables guidance of the lead to a target location within the heart, such as the right ventricle. With reference to FIG. 5, a location for placement of the distal end structure 322 of the lead 304b is at the interface between the diaphragm 106 and the lower wall 504 of the right ventricular of the heart 104. A preferred location is at the apex 506 of the right ventricle.

While the transcardiac lead 304b is shown and described with reference to implant in the right ventricle, the lead may be implanted in any heart chamber that is adjacent to the diaphragm 106. For example, with reference to FIG. 1B, the transcardiac lead 304b may be implanted in the right atrium or the left ventricle, each of which interface closely with the diaphragm 106. With reference to FIGS. 3B and 4, the transcardiac lead 304b may include a mechanism 426 at the distal end of the lead that facilitates penetration through a wall of cardiac tissue 404 and the diaphragm 106. The mechanism 426 may be a screw or punch mechanism. The transcardiac lead 304b further includes a mechanism 428, e.g., a pull wire, configured to transition the distal end structure 322 from the collapsed state shown in FIG. 3A, to the expanded state shown in FIG. 4., and to lock the distal end structure in an expanded state.

Returning to FIG. 3A, in another embodiment, the lead 306 that includes the ADS therapy mechanism 100 and the cardiac event sensor 103 is an endocardial lead configured to be implanted in the right atrium of a heart. In this embodiment the ADS therapy mechanism 100 includes one or more electrodes 332, 334 that enable the delivery of diaphragmatic stimulation pulses to muscles of the diaphragm. In some configurations, these same electrodes 332, 334 also enable the sensing of electrical activity of the heart, and thereby function as the cardiac event sensor 103. In other configurations, the cardiac event sensor 103 may comprise electrodes different from the electrodes of the ADS therapy mechanism 100.

The ADS therapy mechanism 100 may also include a mechanical transducer 336 that enables the delivery of diaphragmatic mechanical pulses to the diaphragm. The mechanical transducer 336 may also function to sense mechanical motion/acceleration in order to monitor the lead movement/acceleration and thereby provide a signal which can be used to confirm effectiveness of the ADS therapy to capture the diaphragm. Alternatively, the ADS therapy mechanism 100 may include a separate mechanical transducer, e.g., motion sensor (not shown), that senses mechanical motion/acceleration in order to monitor the lead movement/acceleration. These components, e.g., electrodes, mechanical transducer, motion sensor, are electrically coupled to a connector (not shown) at the proximal end 338 of the lead through wires extending through a lead body 340.

In cases where the multi-piece IMB 300 is configured to deliver cardiac therapy to the heart, the endocardial lead 306 also includes a CRM therapy mechanism 101. The CRM therapy mechanism 101 may include one or more electrodes. In some configurations, the electrodes of the CRM therapy mechanism 101 may be the electrodes 332, 334 of the ADS therapy mechanism 100. In other configurations, the electrodes of the CRM therapy mechanism 101 may be the electrodes of the cardiac event sensor 103. In other configurations, the electrodes of the CRM therapy mechanism 101 may be electrodes different from the electrodes of the ADS therapy mechanism 100 and the electrodes of the cardiac event sensor 103. In any case, the electrodes of the CRM therapy mechanism 101 are configured to deliver cardiac therapies, such as bradycardia pacing, anti-tachycardia pacing.

Continuing with FIG. 3A, in another embodiment, the lead 308 that includes the ADS therapy mechanism 100 and the cardiac event sensor 103 is an endocardial lead configured to be implanted in the coronary sinus of a heart. In this embodiment the ADS therapy mechanism 100 includes one or more electrodes 342, 344, 346 that enable the delivery of diaphragmatic stimulation pulses to muscles of the diaphragm or far-field stimulation to the phrenic nerve that induces movement of the diaphragm. In some configurations, these same electrodes 342, 344 also enable the sensing of electrical activity of the heart, and thereby function as the cardiac event sensor 103. In other configurations, the cardiac event sensor 103 may comprise electrodes different from the electrodes of the ADS therapy mechanism 100.

The ADS therapy mechanism 100 may also include a mechanical transducer 348 that enables the delivery of diaphragmatic mechanical pulses to the diaphragm. The mechanical transducer 348 may also function to sense mechanical motion/acceleration in order to monitor the lead movement/acceleration and thereby provide a signal which can be used to confirm effectiveness of the ADS therapy to capture the diaphragm. Alternatively, the ADS therapy mechanism may include a separate mechanical transducer, e.g., motion sensor (not shown), that senses mechanical motion/acceleration in order to monitor the lead movement/acceleration. These components, e.g., electrodes, mechanical transducer, motion sensor, are electrically coupled to a connector (not shown) at the proximal end 350 of the endocardial lead 308 through wires extending through a lead body 352.

In cases where the multi-piece IMB 300 is configured to deliver cardiac therapy to the heart, the endocardial lead 308 also includes a CRM therapy mechanism 101. The CRM therapy mechanism 101 may include one or more electrodes. In some configurations, the electrodes of the CRM therapy mechanism 101 may be the same electrodes 342, 344, 346 of the ADS therapy mechanism 100. In other configurations, the electrodes of the CRM therapy mechanism 101 may be electrodes of the cardiac event sensor 103. In other configurations, the electrodes of the CRM therapy mechanism 101 may be electrodes different from the electrodes of the ADS therapy mechanism 100 and the electrodes of the cardiac event sensor 103. In any case, the electrodes of the CRM therapy mechanism 101 are configured to deliver cardiac therapies, such as bradycardia pacing, anti-tachycardia pacing.

With reference to FIG. 3B, the leads 304a, 306, 308 of FIG. 3A are shown implanted in a heart as part of an IMD 300 suitable for sensing cardiac activity and delivering multi-chamber cardiac therapy including cardioversion, defibrillation and pacing stimulation. The IMB 300 may be a cardiac pacemaker, an ICD, a defibrillator, an ICD coupled with a pacemaker, a cardiac resynchronization therapy (CRT) pacemaker, a cardiac resynchronization therapy defibrillator (CRT-D), and the like.

The IMD 300 is configured for placement in electrical communication with the right side of a patient's heart 104 by way of a right atrial (RA) endocardial lead 306 and a right ventricular (RV) endocardial lead 304a. The RA endocardial lead 306 is designed for placement in a right atrium and, in this exemplary implementation, includes an atrial tip electrode 332, which typically is implanted in the patient's right atrial appendage, and an atrial ring electrode 334. Accordingly, the RA lead 306 is capable of sensing electrical cardiac signals, and delivering stimulation in the form of pacing therapy to the right side of the heart, and in particular the right atrium.

The RV lead 304a, in this exemplary implementation, includes a RV tip electrode 312, a RV ring electrode 310, a RV coil electrode 320, and a superior vena cava (SVC) coil electrode 354. Typically, the RV lead 304a is designed to be transvenously inserted into the heart 104 to place the RV tip electrode 312 in the right ventricular apex, the RV coil electrode 320 in the right ventricle and the SVC coil electrode 354 in the superior vena cava. Accordingly, the RV lead 304a is capable of sensing electrical cardiac signals, and delivering stimulation in the form of pacing and shock therapy to the right side of the heart, and in particular the right ventricle.

The IMD 300 is in electrical communication with the left side of a patient's heart 104 by way of a coronary sinus (CS) lead 308 designed for placement in the coronary sinus region. As used herein the coronary sinus region refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

The CS endocardial lead 308, in this exemplary implementation, includes a left ventricular (LV) tip electrode 342, a left atrial (LA) ring electrode 344, and a LA coil electrode 346. Typically the CS lead 308 is designed to be transvenously inserted into the heart 104 to access the coronary sinus region so as to place the LV tip electrode 342 adjacent to the left ventricle, the LA ring electrode 344 and the LA coil electrode 346 adjacent to the left atrium. Accordingly, the CS endocardial lead 308 is capable of sensing electrical cardiac signals, and delivering stimulation in the form of pacing and shock therapy to the left side of the heart.

Although three leads are shown in FIG. 3B, fewer or more leads (with one or more pacing, sensing and/or shocking electrodes) may be used in order to efficiently and effectively provide pacing stimulation, cardioversion and/or defibrillation. Furthermore, an individual lead may include additional electrodes. For example, the CS endocardial lead 308 may include additional ring electrodes spaced apart between the LV tip electrode 342 and the LA coil electrode 346.

Single-piece Implantable Medical Device

Figure 6A:
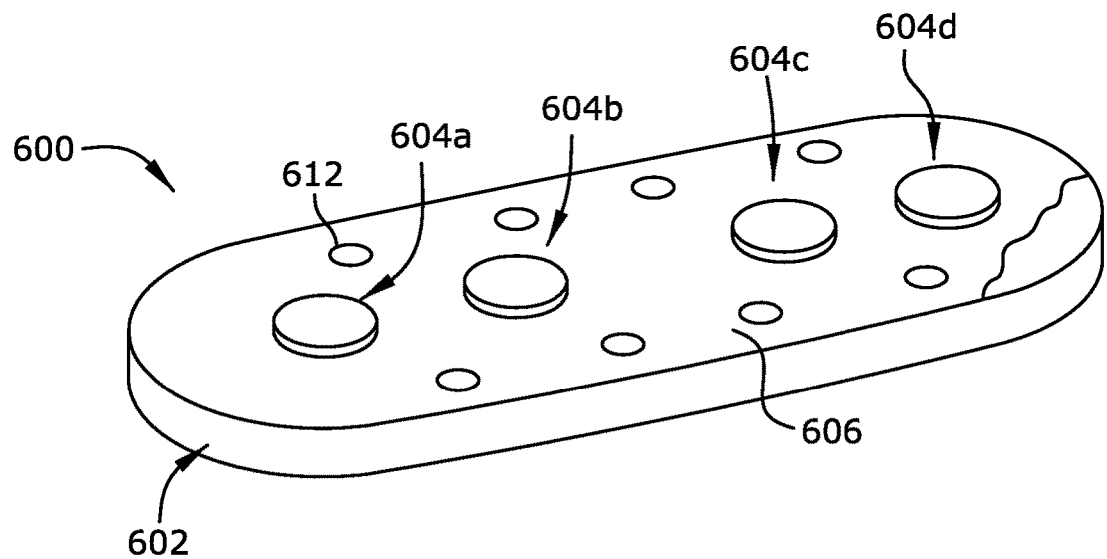
FIGS. 6A and 6B are illustrations of a single-piece embodiment of an implantable medical device that carries an ADS therapy mechanism and a CRM therapy mechanism.
Figure 6B:
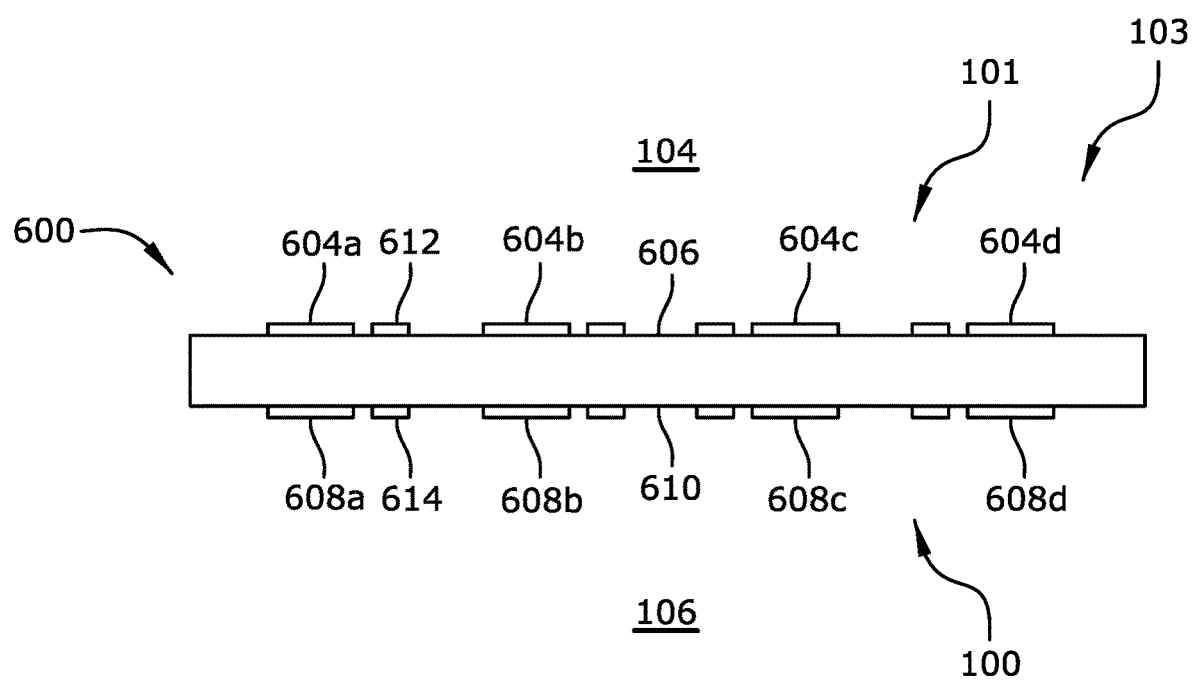

FIGS. 6A and 6B illustrate a single-piece IMD 600. With reference to FIG. 1A, the IMB 600 may be configured to be implanted at an interface area 102 of the right ventricle of a heart 104 and a diaphragm 106. The IMD 600 includes the ADS therapy mechanism 100 and the cardiac event sensor 103. The IMB 600 includes a housing 602 with a first plurality of spaced-apart electrodes 604a-604d associated with a first surface 606 of the housing, and a second plurality of spaced-apart electrodes 608a-608d associated with a second surface 610 of the housing.

The single-piece IMD 600 is configured so that one of the plurality of electrodes 604a-604d may be placed adjacent the heart 104, and the other of the plurality of electrodes 608a-608d may be placed adjacent the diaphragm 106. The electrodes 604a-604d adjacent the heart 104 form a cardiac event sensor 103 that enables bipolar sensing of electrical activity of the heart between pairs of electrodes. The electrodes 608a-608d adjacent the diaphragm 106 form an ADS therapy mechanism 100 that enables the delivery of diaphragmatic stimulation directly to the diaphragm 106 through a pair of electrodes. Various electrode configurations for cardiac sensing and diaphragm pacing may be tested during implant of the single-piece IMD 600 and changed later via device programming if needed.

In cases where the single-piece IMD 600 is configured to deliver cardiac therapy to the heart, the IMD also includes a CRM therapy mechanism 101. The CRM therapy mechanism 101 may include one or more pacing electrodes configured to deliver cardiac therapies, such as bradycardia pacing, anti-tachycardia pacing. These pacing electrodes may be one or more of the plurality of electrodes 604a-604d placed adjacent the heart 104. These pacing electrodes may include an additional electrode.

While the IMD 600 illustrated in FIGS. 6A and 6B is formed in the shape of an elongated disk, the IMD may have other form factors, including for example, a tube. The leadless IMD 600 may have a length of about 1.25-inches, a width of about 0.5-inches, and a thickness of about 0.125-inches.

The IMD 600 may include a fixation mechanism configured to secure the housing 602 in place relative to the heart and the diaphragm. To this end, a first plurality of spaced-apart mechanical elements 612 may be associated with the first surface 606 of the housing, and a second plurality of spaced-apart mechanical elements 614 may be associated with a second surface 610 of the housing. The mechanical elements 612, 614 are configured to facilitate quick deployment and sutureless anchoring of the IMD 600 to one or both of a surface adjacent the heart a surface adjacent the diaphragm. For example, the mechanical elements 612 on the first surface 606 of the housing 602 may comprise spring-loaded or otherwise mechanically activated wires/pins/hooks configured to extend into the pericardium of the heart. Likewise, the mechanical elements 614 on the second surface 610 of the housing 602 may comprise spring-loaded or otherwise mechanically activated wires/pins/hooks configured to extend into the superior side of the diaphragm.

An introducer tool enables insertion and easy deployment of the IMD 600 in a location between the right ventricle of a heart 104 and a diaphragm 106, with the preferred implant location being underneath the heart at the right ventricular lower septum/apex. The tool may include a trocar or syringe-like structure tailored for sub-xiphoid or other adequate access, and a built-in camera/light system to facilitate safe protrusion, device insertion and anchoring.

Implantable Medical Devices with ADS Therapy

Figure 7A:
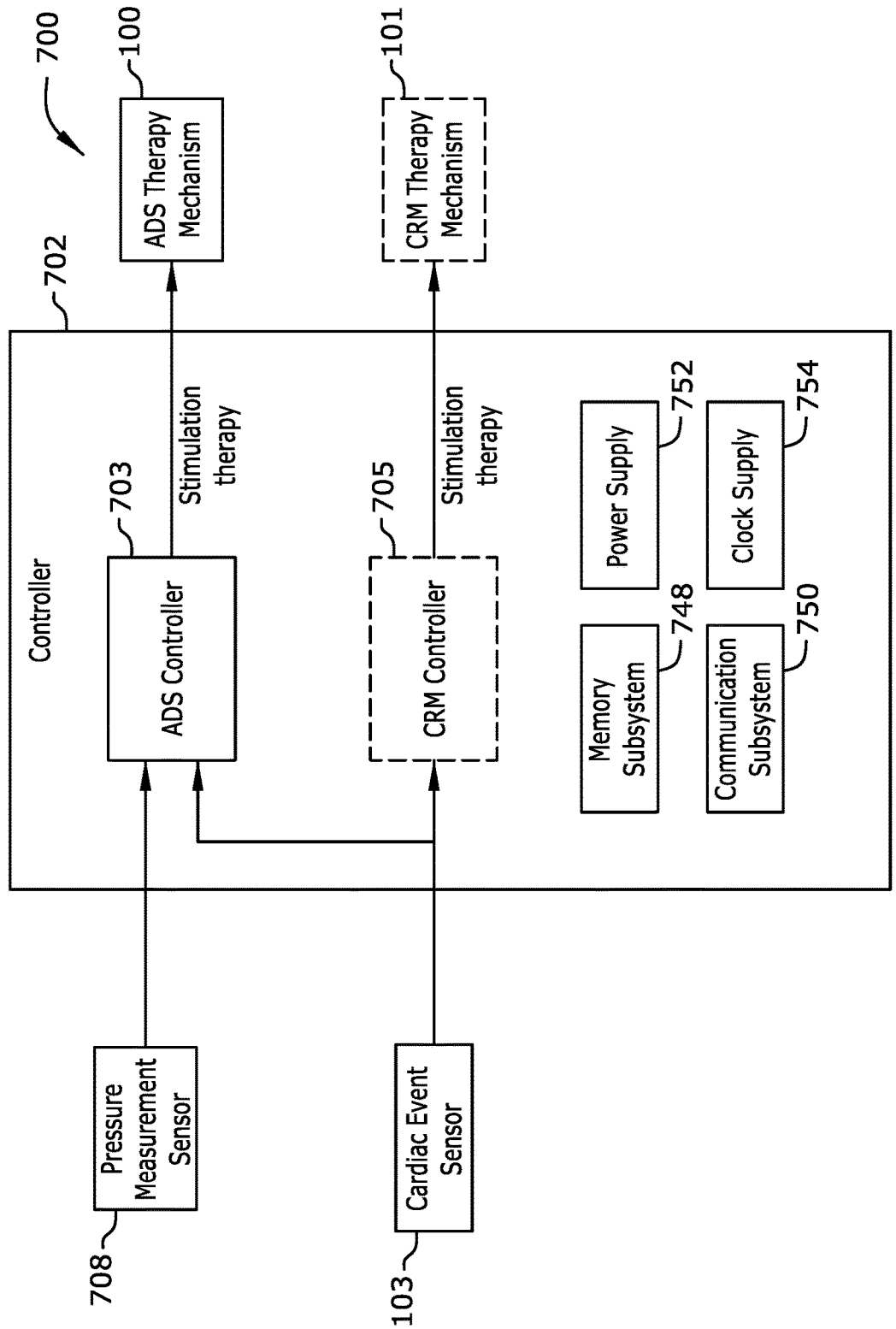
FIG. 7A is a general block diagram of an implantable medical device with an ADS controller configured to deliver diaphragmatic stimulation through an ADS therapy mechanism, and an optional CRM controller configured to deliver cardiac therapy through a CRM therapy mechanism.
Figure 7B:
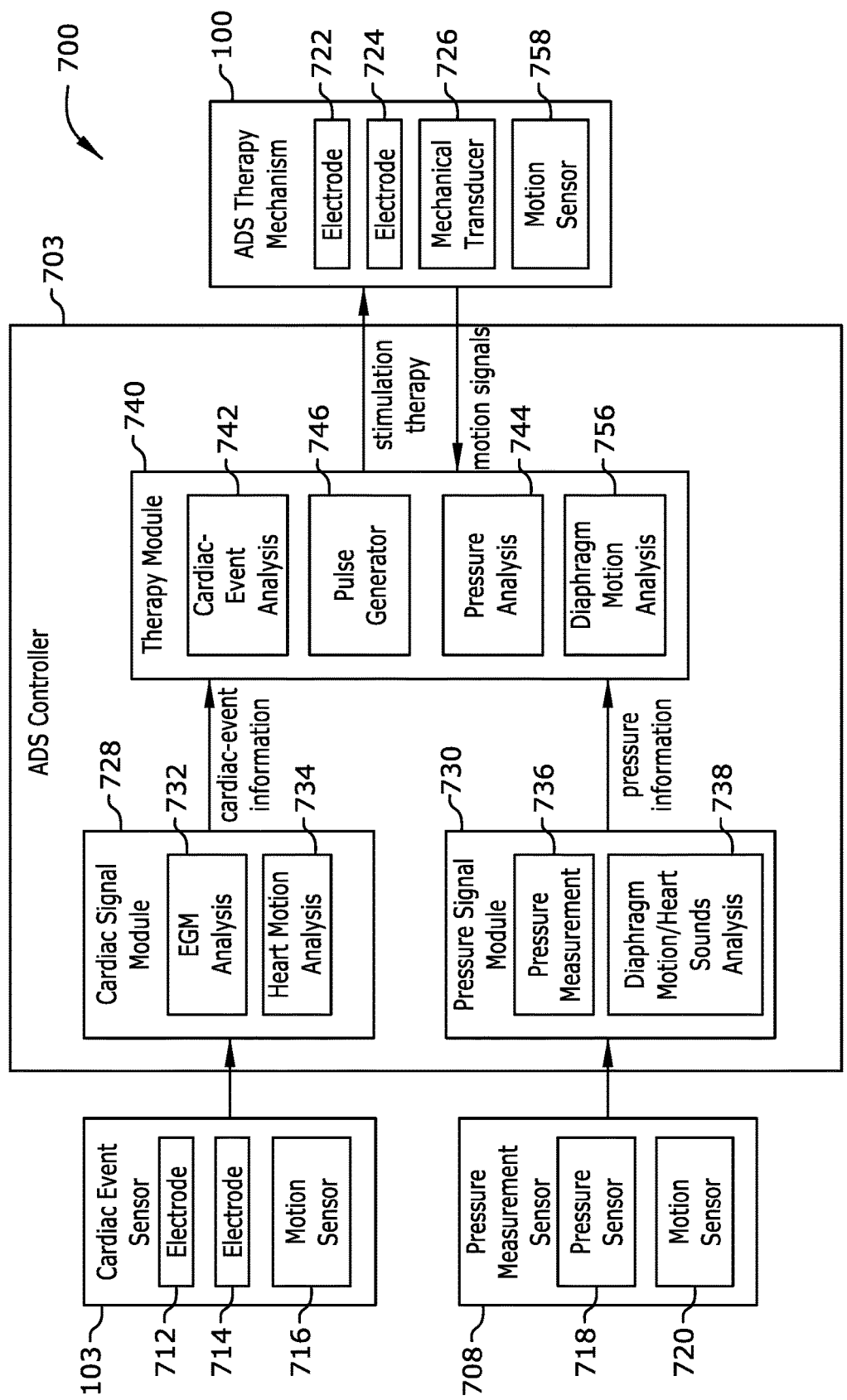
FIG. 7B is a block diagram illustrating details of the ADS controller of FIG. 7A.
Figure 7C:
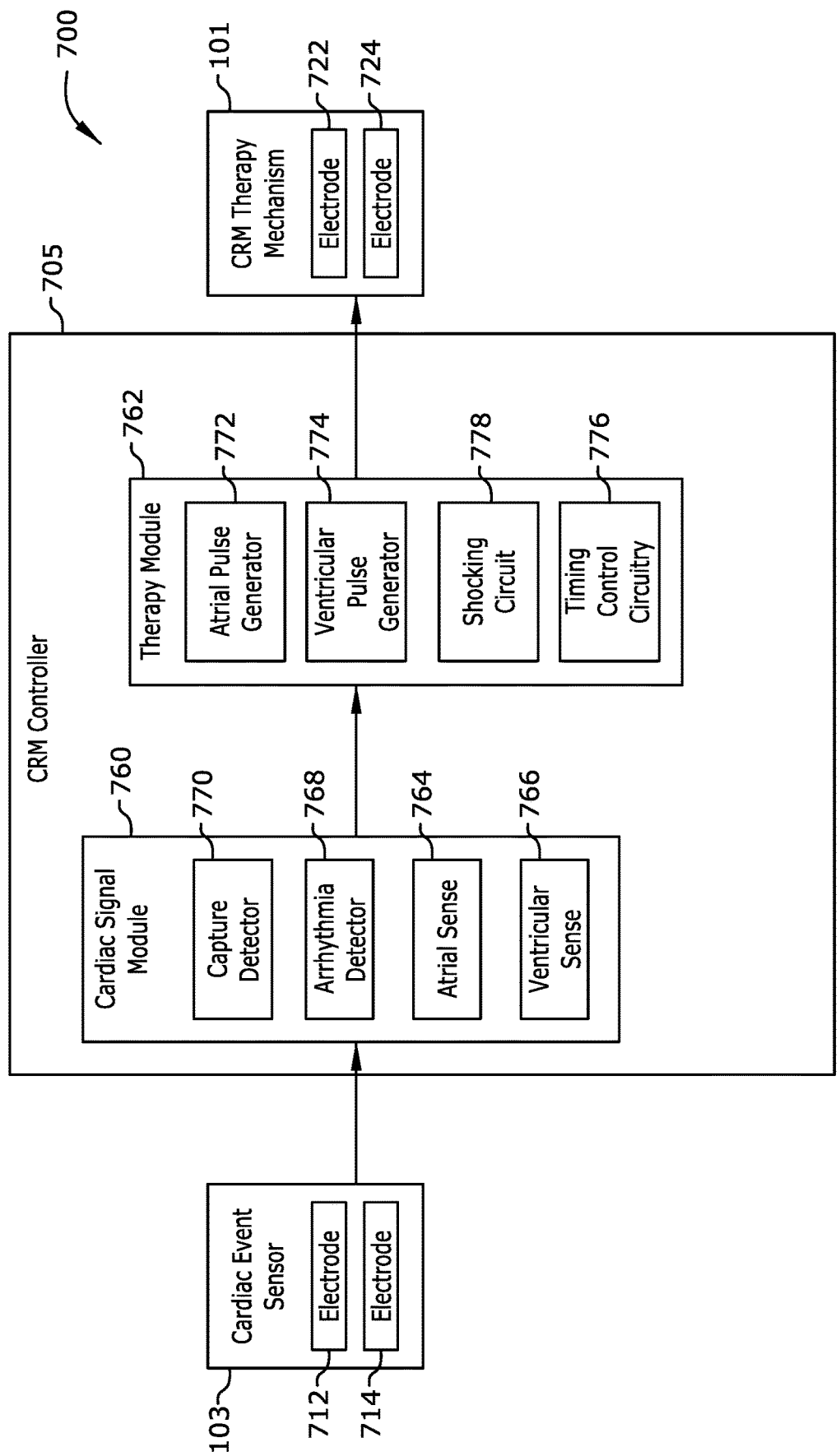
FIG. 7C is a block diagram illustrating details of the optional CRM controller of FIG. 7A.

FIGS. 7A, 7B and 7C are block diagrams of an IMD 700 configured to affect pressures within the intrathoracic cavity through delivery of ADS therapy, either alone or in combination with cardiac therapy. The IMD 700 includes a controller 702, a cardiac event sensor 103, a pressure measurement sensor 708, an ADS therapy mechanism 100, and an optional CRM therapy mechanism 101, each of which may be coupled for interaction with the controller, either through a wired connection or through a wireless connection. The controller 702 includes an ADS controller 703, and may include a CRM controller 705.

With reference to FIG. 7B, the ADS controller 703 includes a cardiac signal module 728, a pressure signal module 730, a therapy module 740, and various other modules. The cardiac event sensor 103 is configured to provide signals to the controller 702 that represent cardiac events. For example, the cardiac event sensor 103 may be one or more electrodes 712, 714 associated with a lead configured to be implanted in or on a heart so that the electrodes are positioned in or on a cardiac structure, e.g., heart, pericardium, great artery and vein, to sense electrical signals representative of cardiac events and to provide the signals to the ADS controller 703. Alternatively, the cardiac event sensor 103 may be one or more electrodes 712, 714 associated with a single-piece device configured to be implanted at a location between the heart and the diaphragm so that the electrodes are positioned on or adjacent to a cardiac structure, e.g. heart, pericardium, great artery and vein, to sense electrical signals representative of cardiac events and to provide the signals to the ADS controller 703.

The cardiac event sensor 103 may also be a motion sensor 716 associated with a lead configured to be implanted in or on a heart so that the motion sensor is positioned in or on a cardiac structure, e.g., heart, pericardium, great artery and vein, to sense motion of the heart or to sense heart sounds, and to output electrical signals representative of such motion. Alternatively, the motion sensor 716 may be associated with a single-piece device configured to be implanted at a location between the heart and the diaphragm so that the motion sensor is positioned on or adjacent to a cardiac structure, e.g. heart, pericardium, great artery and vein, to sense motion of the heart or to sense heart sounds, and to output electrical signals representative of such motion. The motion sensor 716 may be, for example, an accelerometer (such as a multi-axial e.g., three-dimensional, accelerometer) that provides signals related to heart movement, or an acoustic transducer that provides signals related to heart sounds.

The pressure measurement sensor 708 is configured to provide signals to the controller 702 that represent one or more pressures within the intrathoracic cavity. "Pressures within the intrathoracic cavity" may include an intrathoracic pressure obtained directly through a pressure sensor placed in the open space of the intrathoracic cavity and outside of any intrathoracic structures, e.g. heart, pericardium, great arteries and veins, within the cavity. "Pressures within the intrathoracic cavity" may also include a measure of intrathoracic pressure obtained indirectly, for example, through an accelerometer placed outside of the intrathoracic cavity that provides a measure indicative of, or correlated with, intrathoracic pressure. "Pressures within the intrathoracic cavity" may also include pressures associated with intrathoracic structures like the heart, pericardium, great arteries and veins. For example, these "pressures within the intrathoracic cavity" may include right atrial pressure, right ventricular pressure, left ventricular pressure, and aortic pressure.

The pressure measurement sensor 708 may be one or more pressure sensors 718 configured to be positioned in the open space of the intrathoracic cavity, or in, on, or adjacent an intrathoracic structure, e.g. heart, pericardium, great artery and vein, within the cavity, and configured to output electrical signals representative of pressure. To these ends, the one or more pressure sensors 718 may be associated with a lead configured to be implanted in or on a heart so that the motion sensor is positioned in or on a cardiac structure, e.g., heart, pericardium, great artery and vein, to provide signals sensed by the one or more pressure sensors to the ADS controller 703. For example, the pressure sensor 718 may be included in a device configured to be implanted: 1) in the right atrium to obtain right-atrial pressure signals, 2) in the right ventricle to obtain right ventricular pressures, 3) in the right ventricle to obtain surrogates of pulmonary artery pressure, or 4) within the pulmonary artery itself. Alternatively, the pressure measurement sensor 708 may be associated with a single-piece device configured to be implanted at a location between the heart and the diaphragm so that the pressure measurement sensor is positioned on or adjacent to a cardiac structure, e.g. heart, pericardium, great artery and vein, to provide signals sensed by the one or more pressure sensors to the ADS controller 703.

The pressure measurement sensor 708 may also be a motion sensor 720 configured to provides signals indicative of, or that correlate to, intrathoracic pressure. For example, the motion sensor 720 may be an accelerometer configured to be positioned on or near a diaphragm to sense motion of the diaphragm, and to output electrical signals representative of such motion to the controller 702. The motion sensor 720 may also be an accelerometer or acoustic transducer configured to be positioned within the patient to sense sounds associated with cardiac function, and to output electrical signals representative of such sounds. Fluctuations in these electrical signals correlate to changes in intrathoracic pressure associated with respiration cycles. Alternatively, the motion sensor 720 may be an impedance/conductance sensor in the form of a pair of electrodes configured to be positioned in or on the diaphragm, and to output electrical signals representative of impedance or conductance of diaphragm tissue. Fluctuations in impedance or conductance correlate to changes in expansion and contraction of the diaphragm, which in turn correlate to changes in intrathoracic pressure associated with respiration cycles.

The ADS therapy mechanism 100 is configured to apply diaphragmatic stimulation, either directly to the diaphragm or through far-field stimulation of the phrenic nerve, to cause asymptomatic, transient, partial contraction of the diaphragm. As previously mentioned, a "transient" contraction of the diaphragm is a short, twitching, caudal followed by cranial motion of the diaphragm that lasts in range of 60 to 180 msec., and is typically about 100 msec. A "partial" contraction of the diaphragm is the part of the diaphragm (less than the entirety of the diaphragm) that exhibits a "transient" contraction. The stimulation is characterized by a set of stimulation parameters that induce a partial contraction of the diaphragm that does not affect respiration. More specifically, the stimulation is configured such that the diaphragm does not contract to a level that induces inspiration.

The ADS therapy mechanism 100 may be one or more electrodes 722, 724 associated with a lead configured to be implanted in or on a heart so that the electrodes are positioned in or on a cardiac structure, e.g., heart, pericardium, great artery and vein, to deliver diaphragmatic stimulation in the form of electrical stimulation pulses. For example, with reference to FIG. 3B, the one or more electrodes 722, 724 may be associated with an endocardial lead 304a, 306, 308. Alternatively, the one or more electrodes 722, 724 may be associated with a lead configured to be implanted in or on a heart so that the electrodes are positioned in or on the diaphragm to deliver diaphragmatic stimulation. For example, with reference to FIG. 4, the one or more electrodes 722, 724 may be associated with a transcardiac lead 304b. Alternatively, the one or more electrodes 722, 724 may be associated with device configured to be implanted at a location between the heart and the diaphragm so that the electrodes are positioned on or adjacent to the diaphragm to deliver diaphragmatic stimulation. For example, with reference to FIG. 6, the one or more electrodes 722, 724 may be associated with a single-piece IMD 600.

The ADS therapy mechanism 100 may include a mechanical transducer 726 that enables the delivery of diaphragmatic mechanical pulses to muscles of the diaphragm. The mechanical transducer 726 may be, for example, an acoustic transducer configured to be positioned on or near a diaphragm. The mechanical transducer 726 may be configured to output mechanical energy to the diaphragm that causes transient movements of the diaphragm. The mechanical transducer 726 may also be configured to sense motion of the diaphragm, and to output electrical signals representative of such motion to the ADS controller 703. The signal may be used as a feedback signal to confirm that the ADS therapy effectively captured the diaphragm. Alternatively, the ADS therapy mechanism may include a separate motion sensor 758, e.g., accelerometer, that senses sense motion of the diaphragm and provides diaphragm capture confirmation.

The mechanical transducer 726 and the motion sensor 758 may be associated with a lead configured to be implanted in or on a heart so that the electrodes are positioned in or on a cardiac structure, e.g., heart, pericardium, great artery and vein, to deliver diaphragmatic stimulation in the form of electrical stimulation pulses. For example, with reference to FIG. 3B, the mechanical transducer 726 and the motion sensor 758 may be associated with an endocardial lead 304a, 306, 308. Alternatively, the mechanical transducer 726 and motion sensor 758 may be associated with a lead configured to be implanted in or on a heart so that the electrodes are positioned in or on the diaphragm to deliver diaphragmatic stimulation. For example, with reference to FIG. 4, the mechanical transducer 726 and the motion sensor 758 may be associated with a transcardiac lead 304b. Alternatively, the mechanical transducer 726 and motion sensor 758 may be associated with device configured to be implanted at a location between the heart and the diaphragm so that the electrodes are positioned on or adjacent to the diaphragm to deliver diaphragmatic stimulation. For example, with reference to FIG. 6, the mechanical transducer 726 and the motion sensor 758 may be associated with a single-piece IMD 600.

Regarding the physical structure of the IMD 700, while the foregoing functional description of the IMD describes separate pairs of electrodes 712, 714 and 722, 724, respectively associated with the cardiac event sensor 103 and the ADS therapy mechanism 100, a configuration of the IMD may include a single pair of electrodes configured to perform dual functions. That is, the IMD 700 may include a single pair of electrodes configured to both sense cardiac electrical activity and to deliver electrical diaphragmatic stimulation. In this configuration, the controller 702 may include an electrode interface that is configured to switch the connection of the electrodes between the cardiac event sensor 103 and the ADS therapy mechanism 100 as needed. The electrode interface may also provide other features, capabilities, or aspects, including but not limited to amplification, isolation, and charge-balancing functions, that are required for a proper interface between the electrodes and diaphragm tissue.

Similarly, the respective functions of the separate motion sensors 716, 720, 758 and the mechanical transducer 726 referenced with respect to the cardiac event sensor 103, the pressure measurement sensor 708, and the ADS therapy mechanism 100 may be provided by a common motion sensor. In this configuration, the ADS controller 703 may include sensor interface that is configured to switch the connection of the common sensor between the cardiac event sensor 103, the pressure measurement sensor 708, and the ADS therapy mechanism 100 if needed. The sensor interface may also provide other features, capabilities, or aspects, including but not limited to amplification, isolation, that are required for a proper interface between the sensor and diaphragm tissue.

Considering the ADS controller 703 in more detail, the cardiac signal module 728 of the controller receives signals from the cardiac event sensor 103, and is configured to process the signals to detect cardiac events of interest. For example, the cardiac signal module 728 may be configured to detect one or more of an electrical cardiac event, such as an intrinsic ventricular depolarization, a ventricular pacing spike, an evoked ventricular depolarization, an intrinsic atrial depolarization, a atrial pacing spike, an evoked atrial depolarization, and 2) a mechanical cardiac event, such as a ventricular contraction represented by an Si sound. Information corresponding to detected cardiac events is provided to the therapy module 740, which in turn processes the cardiac-event information to determine or adjust one or more parameters of a stimulation therapy, and to trigger the delivery of diaphragmatic stimulation.

With respect to electrical cardiac events, the cardiac signal module 728 may include an electrogram (EGM) analysis module 732 adapted to receive electrical signals from the electrodes 712, 714 of the cardiac event sensor 103, and to process the electrical signals to detect cardiac events of interest. The EGM analysis module 732 may be configured to process a cardiac electrical activity signal, e.g., an EGM signal, to detect cardiac events corresponding to atrial events, such as P waves, or ventricular events, such as R waves, QRS complexes, or T waves.

Regarding mechanical cardiac events, the cardiac signal module 728 may include a heart motion/sounds analysis module 734 for analyzing mechanical motion of the heart. The heart motion/sounds analysis module 734 is adapted to receive signals from the motion sensor 716 of the cardiac event sensor 103, and to detect a cardiac event of interest. As previously mentioned, the motion sensor 716 may be, for example, an accelerometer or acoustic transducer, configured to sense a variety of mechanical and sound activities, such as diaphragm motion and heart sounds. Heart sound signals obtained through the accelerometer may be processed by the heart motion/sounds analysis module 734 to detect cardiac events.

The pressure signal module 730 of the ADS controller 703 receives signals from the pressure measurement sensor 708 and is configured to process the signals for purposes of detecting a pressure event of interest or deriving a pressure measure of interest. For example, regarding measures of interest, the pressure signal module 730 may process signals from a pressure sensor 718 to determine pressure measurements under different therapy conditions, e.g., with diaphragmatic stimulation on, and with diaphragmatic stimulation off, or under different stimulation settings. The pressure signal module 730 may also process signals from a pressure sensor 718 to determine pressure measurements at different times, e.g., at or near delivery of a stimulation pulse, and at or near an occurrence of a particular cardiac event. Regarding events of interest, the pressure signal module 730 may process signals from a motion sensor 720 to detect respiration cycles and to identify one or more events of interest within the cycle, such as end inspiration. Information corresponding to detected events of interest and measures of interest, collectively referred to as pressure information, is provided to the therapy module 740. The therapy module 740, in turn, processes the pressure information to determine whether an adjustment to one or more parameters of a stimulation therapy is warranted.

Regarding the processing of signals from a pressure sensor 718, the pressure signal module 730 may include a pressure measurement module 736 for analyzing pressures within the intrathoracic cavity. The pressure measurement module 736 is adapted to receive signals from the pressure sensor 718 of the pressure measurement sensor 708. As previously described, the pressure sensor 718 may be a configured to be placed in the open space of the intrathoracic cavity and outside of any intrathoracic structures, e.g. heart, pericardium, great arteries and veins, within the cavity—to thereby provide a signal representing intrathoracic pressure. Alternatively, the pressure sensor 718 may be configured to be placed in, on, or adjacent an intrathoracic structure, e.g. heart, pericardium, great artery and vein, within the cavity. For example, the pressure sensor 718 may be configured to be placed in, on, or adjacent to one of the right atrium, the right ventricle, the left ventricle, the aorta, and the pulmonary artery—to thereby provide a corresponding signal presenting right atrial pressure, right ventricular pressure, left ventricular pressure, aortic pressure, or pulmonary artery pressure.

The pressure measurement module 736 is further adapted to process signals obtained from the pressure sensor 718 to derive pressure measures of interest. The pressure measurement is provided to the therapy module 740, where it is further processed to determine if stimulation therapy may be improved to provide a more desirable outcome. For example, different measures of intrathoracic pressure may be obtained for different stimulation therapies, each defined by a different set of stimulation parameter values, to determine which set of stimulation parameters provides the best measure of intrathoracic pressure. In another example, the measure of intrathoracic pressure may be compared to a predetermine threshold value, to determine if one or more of the stimulation parameters should be adjusted in an attempt to obtain, or at least more closely approach, the threshold value.

Regarding the processing of signals from a motion sensor 720, the pressure signal module 730 may include a diaphragm motion and heart sounds analysis module 738 for analyzing one or more of motion of the diaphragm and sounds associated with the heart. The diaphragm motion and heart sounds analysis module 738 is adapted to receive signals from the motion sensor 720 of the pressure measurement sensor 708, and to detect a pressure event of interest. As previously described, the motion sensor 720 may be an accelerometer configured to be positioned on or near a diaphragm to sense motion of the diaphragm. The motion sensor 720 may also be an accelerometer or an acoustic transducer configured to be positioned within the patient to sense sounds associated with cardiac function, and to output electrical signals representative of such sounds. Alternatively, the motion sensor 720 may be an impedance/conductance sensor in the form of a pair of electrodes configured to be positioned in or on the diaphragm.

Regarding the therapy module 740, it includes a cardiac-event analysis module 742, a pressure analysis module 744, a pulse generator 746, and a diaphragm motion analysis module 756. The pulse generator 746 is configured to output stimulation therapy to the ADS therapy mechanism 100. The stimulation therapy may be in the form of electrical stimulation, in which case the therapy may be delivered through electrodes 722, 724. The stimulation therapy may be in the form of mechanical stimulation, in which case the therapy may be delivered through a mechanical transducer 726.

The stimulation therapy output by the pulse generator 746 is defined by one or more stimulation parameters. For electrical stimulation, the parameters may include: 1) one or more pulse parameters having a value or setting selected to define a stimulation pulse that induces a transient, partial contraction of the diaphragm, and 2) a timing parameter that controls the timing of the delivery of one or more stimulation pulses. The pulse parameters may include, for example, a pulse waveform type, a pulse amplitude, a pulse duration, and a pulse polarity. The timing parameter may include one or more offset periods or delay periods that define a time between a detected cardiac event and a delivery of an electrical stimulation pulse. For mechanical stimulation, the parameters may include for example, a mechanical pulse waveform type, a mechanical pulse amplitude, a mechanical pulse duration. The timing parameter may include one or more offset periods or delay periods that define a time between a detected cardiac event and a delivery of a mechanical pulse.

With respect to the pulse parameters, a transient, partial contraction of the diaphragm typically entails a very short (only a few tens of milliseconds) pulse-like, biphasic (singular-caudal followed by singular-cranial) asymptomatic motion of the diaphragm. The IMD 700, including in particular the therapy module 740, is configured to generate stimulation pulses that result in very short, biphasic asymptomatic motion of the diaphragm. To this end, the therapy module 740 may be configured to select a setting of square, sinusoidal, triangular, or sawtooth for the pulse waveform type, and to select a setting of positive or negative for the pulse polarity. The therapy module 740 may be further configured to select a value for the pulse amplitude that is between 0.1 volts and 10.0 volts, and to select a value for the pulse duration that is between 0.1 milliseconds and 5 milliseconds.

In cases where far-field stimulation of the phrenic nerve is used to evoke transient contractions of the diaphragm, the pulse parameters may be set toward the upper end of their respective range in order to produce stimulation pulses of sufficient energy to capture the phrenic nerve. For example, the pulse amplitude may be set to a value at the upper end of the 0.1 volts to 10.0 volts range, such as between 5.0 volts and 10.0 volts, and the pulse duration may be set to a value at the upper end of the 0.1 milliseconds to 5 milliseconds range, such as between 2.5 milliseconds and 5 milliseconds.

In cases where far-field stimulation of muscles of the diaphragm is used to evoke transient contractions of the diaphragm, the pulse parameters may be set toward the mid-range of their respective range in order to produce stimulation pulses of sufficient energy to capture the diaphragm while avoiding stimulation of the phrenic nerve. For example, the pulse amplitude may be set to a value at the mid-range of the 0.1 volts to 10.0 volts range, such as between 3 volts and 6 volts, and the pulse duration may be set to a value at the mid-range of the 0.1 milliseconds to 5 milliseconds range, such as between 1.5 milliseconds to 3.0 milliseconds.

In cases where direct stimulation of muscles of the diaphragm is used to evoke transient contractions of the diaphragm, the pulse parameters are set toward the lower end of their respective range in order to produce stimulation pulses of sufficient energy to capture the diaphragm. For example, the pulse amplitude may be set to a value at the lower end of the 0.1 volts to 10.0 volts range, such as between 0.1 volts and 2.5 volts, and the pulse duration may be set to a value at the lower end of the 0.1 milliseconds and 5 milliseconds range, such as between 0.1 milliseconds and 2.0 milliseconds.

Regarding the timing parameter, the therapy module 740 may be configured to determine one or more offset periods or delay periods. The delay period may be based on the time between successive detected cardiac events. For example, the EGM analysis module 732 of the cardiac signal module 728 may be configured to detect ventricular events, e.g., R waves, and to output such detections to the therapy module 740. The cardiac-event analysis module 742 may process the detected ventricular events to determine a statistical measure of time between a number of pairs of successive ventricular events. The cardiac-event analysis module 742 may then determine a delay period based on the statistical measure and an offset relative to the statistical measure, and control the pulse generator 746 to output ADS pulses based on the determined offset period or delay period.

Initial selection of pulse parameter settings and values and the timing parameter by the therapy module 740 may be performed by a physician through an external device, e.g., a programmer. In this case, the external device provides selection commands to the therapy module 740 through a wireless communication link, and the therapy module selects the pulse parameters and timing parameter in accordance with the commands. Alternatively, selection of pulse parameter settings and values and the timing parameter by the therapy module 740 may be automated.

One or more of the stimulation parameters, including timing parameters and pulse parameters, may be adjusted by the therapy module 740. With respect to timing parameters, the rate of electrical stimulation may be adjusted in response to changes in the heart rate of the patient. Accordingly, the rate of delivery of electrical stimulation pulses may range, for example, between 30 pulses per minute (ppm) and 180 ppm, with a typical rate being around 60 ppm. Likewise, a delay period between a detected cardiac event and a delivery of an electrical stimulation pulse may be adjusted based on a running average of time intervals between detected cardiac events. Regarding pulse parameters, the pulse amplitude may be set to a value between 0.1 volts and 10.0 volts, and the pulse width may be set to a value between 0.1 milliseconds and 5 milliseconds. The amplitude may be adjusted, for example, in increments of between 0.1 to 0.5 volts, while the pulse width may be adjusted in increments of between 0.1 to 1.5 milliseconds. The polarity may be changed between a positive polarity and a negative polarity, and the waveform type may be changed from mono-phasic to biphasic, or from a square to a triangular, sinusoidal or sawtooth waveform.

The cardiac-event analysis module 742 is configured to receive cardiac-event information from the cardiac signal module 728 and to process the information to determine the timing parameter. To this end, in one configuration, the cardiac-event analysis module 742 determines a time, relative to a detected cardiac event, at which to deliver a stimulation pulse to the diaphragm. The determined time, referred to as a delay period, may be selected so that the stimulation pulse is delivered just prior to the next expected occurrence of the cardiac event.

The offset periods or delay periods may be based on the time between successive detected cardiac events. For example, the EGM analysis module 732 of the cardiac signal module 728 may be configured to detect ventricular events, e.g., R waves, and to output such detections to the therapy module 740. The cardiac-event analysis module 742 may process the detected ventricular events to determine a statistical measure of time between a number of pairs of successive ventricular events. The cardiac-event analysis module 742 may then determine one or more offset periods or delay periods based on the statistical measure, and control the pulse generator 746 to output stimulation pulses based on the determined offset period or delay period.

The pressure analysis module 744 of the therapy module 740 is configured to receive pressure information, including one or more of a measure of interest, e.g., a pressure measurement, or an event of interest, e.g., end inspiration of a respiration cycle, from the pressure signal module 730. The pressure analysis module 744 is further configured to process the received pressure information to determine if an adjustment of a stimulation parameter is warranted.

In one configuration, the pressure analysis module 744 may receive pressure information corresponding to a measure of interest, and may evaluate the measure of interest against a baseline measure of interest. For example, the received measure of interest may be a measure of an intrathoracic pressure, RA pressure, RV pressure, Ao pressure, or LV pressure at a fiducial point. The pressure analysis module 744 may compare the received measure of interest to the baseline to determine if the comparison outcome is acceptable. If the comparison outcome is not acceptable, the therapy module 740 may adjust one or more stimulation parameters for future stimulation therapy to eventually arrive at a stimulation therapy that results in an acceptable outcome.

In another configuration, the pressure analysis module 744 may receive pressure information corresponding to an occurrence of a pressure event of interest. The pressure event of interest may, for example, relate to respiration cycles of a patient and may be a point of end inspiration within a respiration cycle. In response to the receipt of such pressure information, the pressure analysis module 744 may determine to withhold stimulation therapy or to change one or more stimulation parameters.

The diaphragm motion analysis module 756 of the therapy module 740 is configured to detect motion of the diaphragm. The diaphragm motion analysis module 756 is adapted to receive signals from the mechanical transducer 726 or motion sensor 758 and to detect transient movements of the diaphragm based on the signals. The detection of transient movements of the diaphragm serve as confirmation of effective ADS therapy delivery. As previously described, the mechanical transducer 726 and motion sensor 758 may be an accelerometer or an acoustic transducer configured to be positioned on or near a diaphragm to sense motion of the diaphragm.

With reference to FIG. 7C, the CRM controller 705 of the IMD 700 includes a cardiac signal module 760 and a therapy module 762 that enable the IMD to sense and treat both fast and slow arrhythmias with stimulation therapy, including cardioversion, defibrillation, and pacing stimulation. To these ends, one or more cardiac event sensors 103 may be configured to provide signals to the CRM controller 705 corresponding to electrical activity of the heart. For example, the cardiac event sensor 103 may be one or more electrodes 712, 714 associated with a lead configured to be implanted in or on a heart so that the electrodes are positioned in or on a cardiac structure, e.g., heart, pericardium, great artery and vein, to sense electrical signals representative of cardiac events and to provide the signals to the CRM controller 705. Alternatively, the one or more electrodes 712, 714 may be associated with a device configured to be implanted at a location between the heart and the diaphragm so that the electrodes are positioned on or adjacent to a cardiac structure, e.g. heart, pericardium, great artery and vein, to sense electrical signals representative of cardiac events and to provide the signals to the CRM controller 705.

With additional reference to FIG. 3A, a multi-piece IMD 300 may support right atrial sensing through a cardiac event sensor 103, e.g., electrodes 332, 334, associated with a RA endocardial lead 306 configured to be implanted in the right atrium. To support left atrial and left ventricular sensing, a cardiac event sensor 103, e.g., electrodes 342, 344, 346, may be associated with a CS endocardial lead 308 configured to be implanted in the coronary sinus. To support right ventricular sensing, a cardiac event sensor 103, e.g., electrodes 310, 312, 320, may be associated with a right ventricular endocardial lead 304a configured to be implanted in the right ventricle. With reference to FIG. 6A, a single-piece IMD 600 may support right ventricular sensing through a cardiac event sensor 103, e.g., electrodes 608a-608d, associated with a housing surface configured to be placed adjacent the heart in the area of the right ventricle.

The cardiac signal module 760 includes sensing circuitry that is coupled to one or more cardiac event sensors 103. This sensing circuitry may include an atrial sensing circuit 764 and a ventricular sensing circuit 766, each configured to sense electrical cardiac activity through the cardiac event sensor 103. Accordingly, the atrial sensing circuit 764 and ventricular sensing circuit 766 may include dedicated sense amplifiers, multiplexed amplifiers, or shared amplifiers. Each sensing circuit 764, 766 preferably employs one or more low power, precision amplifiers with programmable gain and/or automatic gain control, bandpass filtering, and a threshold detection circuit, as known in the art, to selectively sense the cardiac signal of interest. The outputs of the atrial and ventricular sensing circuits 764, 766 are connected to the therapy module 762, which in turn, is able to trigger or inhibit the delivery of cardiac therapy by the therapy module 762 in a demand fashion in response to the absence or presence of cardiac activity in the appropriate chambers of the heart.

The cardiac signal module 760 may include an arrhythmia detector module 768 that employs one or more algorithms that process sensed cardiac activity to detect arrhythmias. Depending on the detected arrhythmia, the arrhythmia detector module 768 may call for administration of one or more stimulation therapies. For arrhythmia detection, the CRM controller 705 may utilize the atrial and ventricular sensing circuits 764, 766 to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia or of a precursor or other factor that may indicate a risk of or likelihood of an imminent onset of an arrhythmia.

The arrhythmia detector module 768 uses timing intervals between sensed events (e.g., P-waves, R-waves, and depolarization signals associated with fibrillation which are sometimes referred to as "F-waves" or "Fib-waves") to perform one or more comparisons to a predefined rate zone limit (i.e., bradycardia, normal, low rate VT, high rate VT, and fibrillation rate zones) and/or various other characteristics (e.g., sudden onset, stability, physiologic sensors, and morphology, etc.) in order to determine the type of therapy that is desired or needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention. The cardiac signal module 760 further includes a capture detector 770 capable of analyzing information output from the sensing circuits 764, 766 to determine or detect whether and to what degree tissue capture has occurred and to program a pulse, or pulses, in response to such determinations.

The therapy module 762 includes an atrial pulse generator 772 and a ventricular pulse generator 774 configured to generate pacing stimulation pulses for delivery by a CRM therapy mechanism 101. The CRM therapy mechanism 101 may be one or more electrodes 722, 724 associated with a lead configured to be implanted in or on a heart so that the electrodes are positioned in or on a cardiac structure, e.g., heart, pericardium, great artery and vein, to deliver diaphragmatic stimulation in the form of electrical stimulation pulses. Alternatively, the one or more electrodes 722, 724 may be associated with a lead configured to be implanted in or on a heart so that the electrodes are positioned in or on cardiac muscle to deliver cardiac therapy stimulation. Alternatively, the one or more electrodes 712, 714 may be associated with a device configured to be implanted at a location between the heart and the diaphragm so that the electrodes are positioned on or adjacent to the heart to deliver cardiac therapy stimulation.

With additional reference to FIG. 3A, a multi-piece IMD 300 may support right atrial pacing through a CRM therapy mechanism 101, e.g., electrodes 332, 334, associated with a right atrial (RA) endocardial lead 306 configured to be implanted in the right atrium. To support left atrial and left ventricular pacing, a CRM therapy mechanism 101, e.g., electrodes 342, 344, 346, may be associated with a CS endocardial lead 308 configured to be implanted in the coronary sinus. To support right ventricular pacing, a CRM therapy mechanism 101, e.g., electrodes 310, 312, 320, may be associated with a right ventricular endocardial lead 304a configured to be implanted in the right ventricle. With reference to FIG. 6A, a single-piece IMD 600 may support right ventricular pacing through a CRM therapy mechanism 101, e.g., electrodes 604a-604d, associated with housing surface configured to be placed adjacent the heart in the area of the right ventricle.

The therapy module 762 also includes timing control circuitry 776 operative to control the timing of the stimulation pulses (e.g., pacing rate, atrio-ventricular (AV) delay, interatrial conduction (A-A) delay, or interventricular conduction (V-V) delay, etc.) as well as to keep track of the timing of refractory periods, blanking intervals, noise detection windows, evoked response windows, alert intervals, marker channel timing, etc., all of which is well known in the art.

In the case where the IMD 700 is intended to operate as an implantable cardioverter/defibrillator (ICD) device, it detects the occurrence of an arrhythmia, and automatically applies an appropriate therapy to the heart aimed at terminating the detected arrhythmia. Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to 40 J), delivered asynchronously (since R-waves may be too disorganized), and pertaining exclusively to the treatment of fibrillation.

To this end, the therapy module 762 further includes a shocking circuit 778 configured to generate shocking pulses of low (e.g., up to 0.5 J), moderate (e.g., 0.5 J to 10 J), or high energy (e.g., 11 J to 40 J). With reference to FIG. 3B, such shocking pulses may be applied to the patient's heart 104 through at least two shocking electrodes selected from the LA coil electrode 346, the RV coil electrode 320, and/or the SVC coil electrode 354. The housing 302 may act as an active electrode in combination with the RV coil electrode 320, or as part of a split electrical vector using the SVC coil electrode 354 or the LA coil electrode 346 (i.e., using the RV electrode as a common electrode).

Returning to FIG. 7A, the controller 702 includes a memory subsystem 748. The memory subsystem 748 is coupled to the ADS controller 703 and the CRM controller 705, and may receive and store data representative of sensed EGMs, sensed intrathoracic cavity pressure, heart sounds, and sensed cardiovascular pressures, e.g., right ventricular pressures, left ventricular pressure, right atrial pressure, and aortic pressure. The memory subsystem 748 may also receive and store data representative of delivered stimulation therapies, including their associated sets of stimulation parameters and times of delivery.

The controller 702 also includes a communication subsystem 750 that enables communication between the controller and other devices. The communication subsystem 750 may include a telemetry coil enabling transmission and reception of signals, to or from an external apparatus, via inductive coupling. Alternative embodiments of the communication subsystem 750 could use an antenna for an RF link, or a series of low amplitude high frequency electrical pulses emitted by the sensor that do not illicit muscle or nervous activation, detected by sensing electrodes of the stimulating IMB. The controller 702 also includes a power supply 752 that supplies the voltages and currents necessary for each module of the controller, and a clock supply 754 that supplies the modules with any clock and timing signals. The power supply may be rechargeable.

ADS Therapy Delivery

Figure 8:
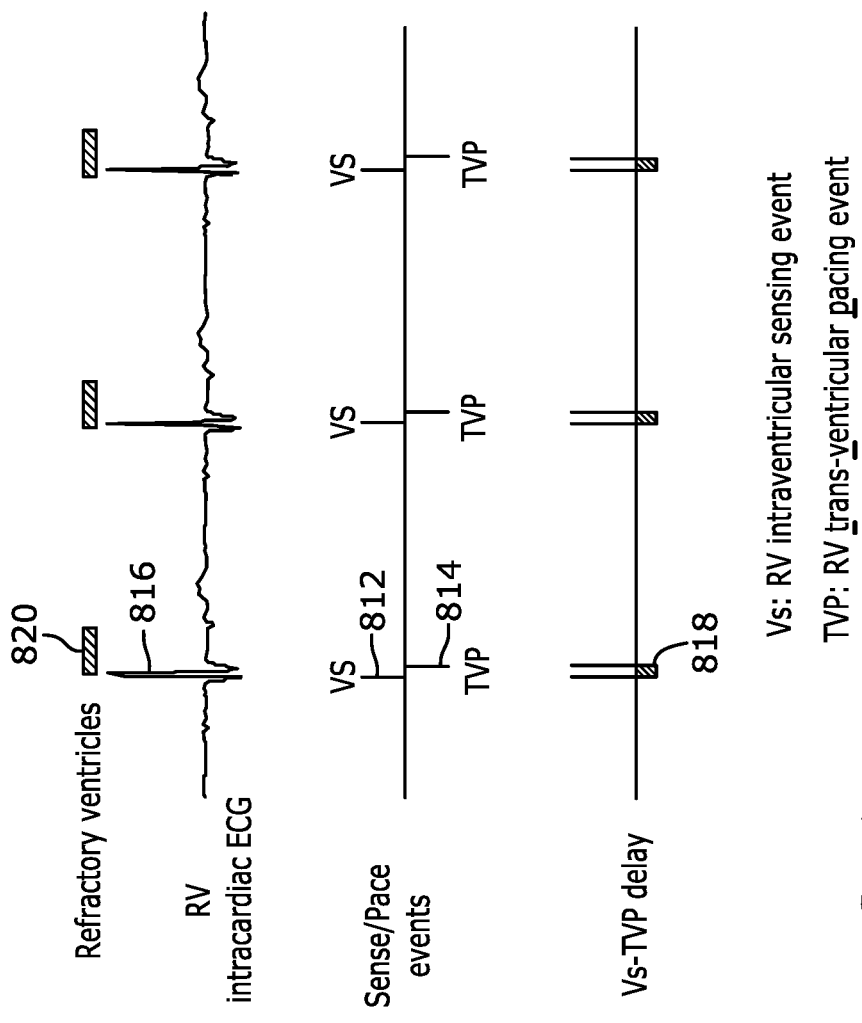
FIG. 8 is a schematic illustration of a transvenous lead implanted in the right ventricle to place an ADS therapy mechanism at an interface of the right ventricular wall and the diaphragm, together with diagrams showing the timing relationship between sensed cardiac events and the delivery of diaphragmatic stimulation.
Figure 8:
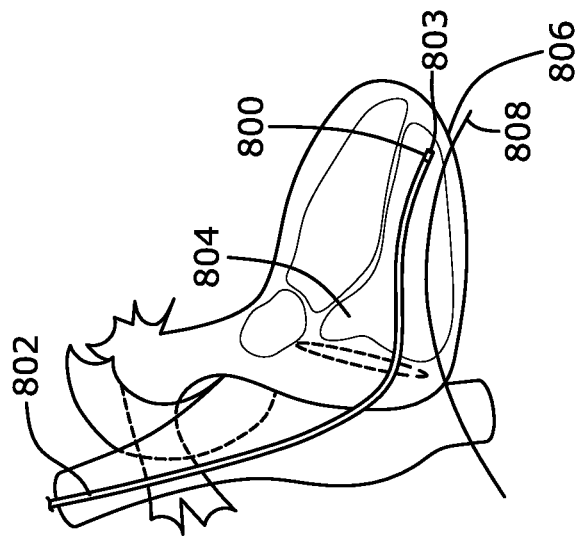

FIG. 8 is a schematic illustration of a transvenous, endocardial lead 802 associated with an IMB corresponding to a standalone ADS therapy device, e.g., a device that only delivers ADS therapy. The lead is a RV endocardial lead 802 configured to be implanted in the right ventricle 804 to place an ADS therapy mechanism 800 and a cardiac event sensor 803 at an interface of the right ventricular wall 806 and the diaphragm 808 for purposes of delivering diaphragmatic stimulation through muscles of the diaphragm. The transvenous lead 802 further includes a cardiac event sensor 803 configured to be placed in, on, or adjacent cardiac tissue to enable the sensing of electrical activity of the heart.

The various time-aligned graphs in FIG. 8 illustrate the relationship between sensed cardiac events 812 and the delivery of diaphragmatic stimulation pulses 814 as enabled by the ADS therapy device. In this embodiment, the IMD senses valid RV events 812 through the cardiac event sensor 803, each event corresponding to an intrinsic ventricular event, e.g., an R wave 816 or a Q wave of an electrocardiogram resulting from an intrinsic, naturally conducting ventricular depolarization. Alternatively, the IMD may sense valid ventricular events through a mechanical sensor of the lead. For example, an accelerometer or acoustic sensor may be used to detect heart sound signals representing contractions of the heart.

Upon sensing a RV event 812, the IMD delivers a diaphragmatic stimulation pulse 814 through the ADS therapy mechanism 800, at the end of a delay period 818. The diaphragmatic stimulation pulse 814 is of sufficient energy to capture the muscles of the diaphragm and to evoke a transient movement of the diaphragm. The delay period 818 is calculated to place delivery of the diaphragmatic stimulation pulse 814 during the refractory period 820 of the ventricle (and the refractory period of the atrium). As such, the diaphragmatic stimulation pulse 814 does not induce an evoked response, e.g. depolarization, in the heart, and only induces a transient contraction of the diaphragm.

A method of ADS therapy through a standalone ADS therapy device includes placing an endocardial or transcardiac pacing/sensing lead(s) in either the right atrium, right ventricle or left ventricle (coronary sinus), and determining a location for placement of an ADS therapy mechanism associated with the lead that allows for close proximity to the diaphragm and/or phrenic nerve. In one embodiment, the location is within right ventricle proximal to the diaphragm and distal to the phrenic nerve. The method further includes coupling the lead to a controller 702 capable of sensing cardiac activity from those lead locations.

The method further includes delivering sufficient energy to initiate transient diaphragmatic muscle contractions by detecting the contraction of the heart (either through an electrical or mechanical sensor); utilizing a programmed and/or calculated time delay ensuring that the heart's atria and ventricle are refractory; and delivering an energy pulse at the end of the calculated/programmed delay sufficient to capture the diaphragmatic muscle in support of an effective ADS therapy.

Figure 9A:
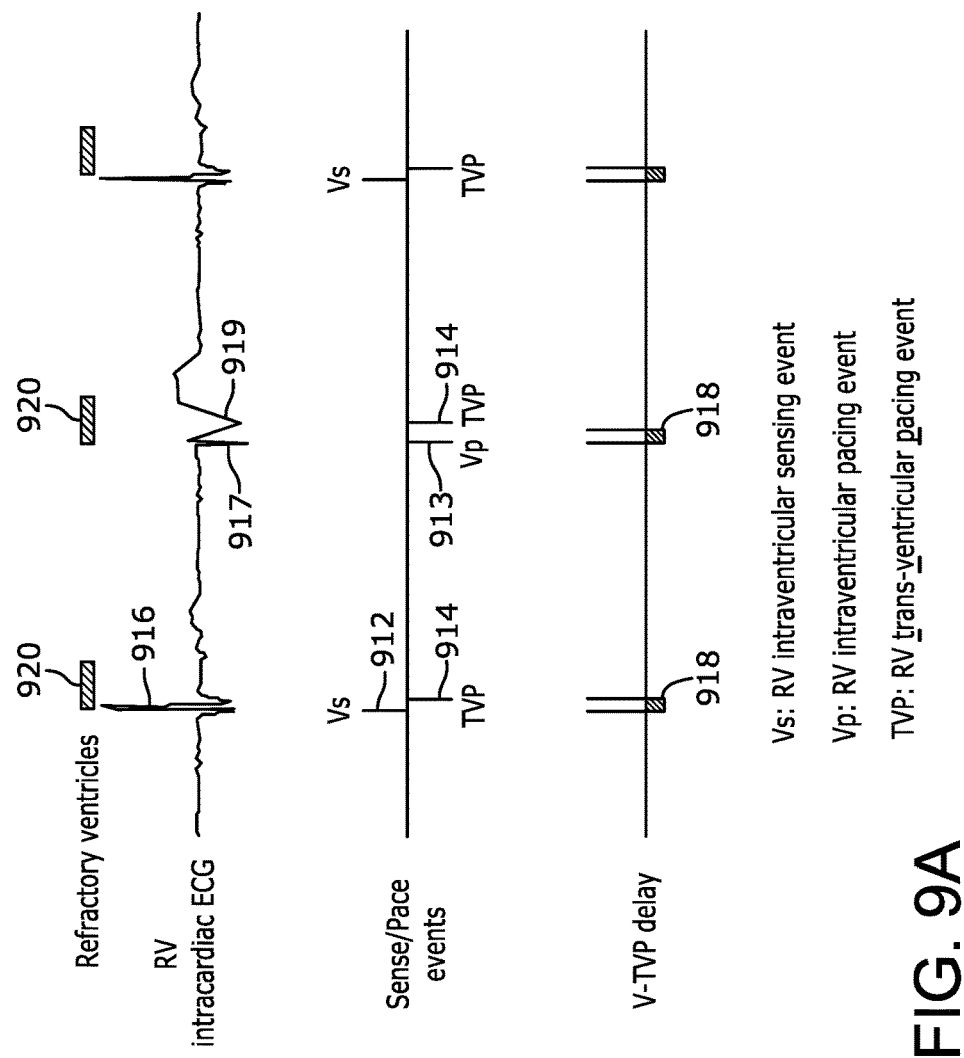
FIG. 9A is a schematic illustration of a transvenous lead implanted in the right ventricle to place an ADS therapy mechanism at an interface of the right ventricular wall and the diaphragm and a CRM therapy mechanism adjacent the right ventricular wall, together with diagrams showing the timing relationship between sensed cardiac events, paced cardiac events, and the delivery of diaphragmatic stimulation.

FIG. 9A is a schematic illustration of a transvenous, endocardial lead 902 associated with an IMD corresponding to a single chamber pacemaker operating in VVI mode and with ADS therapy capability. VVI mode corresponds to ventricular demand pacing, during which the ventricle is paced and sensed, and the pulse generator of the device inhibits pacing output in response to a sensed ventricular event. The lead is a RV endocardial lead 902 configured to be implanted in the right ventricle 904 to place an ADS therapy mechanism 900 at an interface of the right ventricular wall 906 and the diaphragm 908 for purposes of delivering diaphragmatic stimulation through muscles of the diaphragm, and a CRM therapy mechanism 901 adjacent the right ventricular wall for purposes of sensing ventricular events and delivering ventricular pacing pulses as needed. The RV endocardial lead 902 further includes a cardiac event sensor 903 configured to be placed in, on, or adjacent cardiac tissue to enable the sensing of electrical activity of the heart.

The various time-aligned graphs in FIG. 9A illustrate the relationship between sensed cardiac events 912, 913 and the delivery of diaphragmatic stimulation pulses 914 as enabled by the pacemaker. In this embodiment, the IMB senses valid RV events 912, 913 through the cardiac event sensor 903. A sensed right ventricular event 912 may correspond to an intrinsic ventricular event, e.g., an R wave 916 or a Q wave of an electrocardiogram resulting from an intrinsic, naturally conducting ventricular depolarization. A sensed right ventricular event 913 may correspond to a ventricular pacing spike 917 of an electrocardiogram resulting from the delivery of a ventricular pacing stimulus through the CRM therapy mechanism 901, or an evoked ventricular depolarization 919 of an electrocardiogram, which depolarization results from and follows the delivery of a ventricular pacing pulse.

Upon sensing a right ventricular event 912, 913 the IMB delivers a diaphragmatic stimulation pulse 914, through the ADS therapy mechanism 900, at the end of a delay period 918. The delay period 918 is calculated to place delivery of the diaphragmatic stimulation pulse 914 in the refractory period 920 of the ventricle. As such, the diaphragmatic stimulation pulse 914 does not induce an evoked response, e.g. depolarization, in the heart, and only induces a transient contraction of the diaphragm.

Figure 9B:
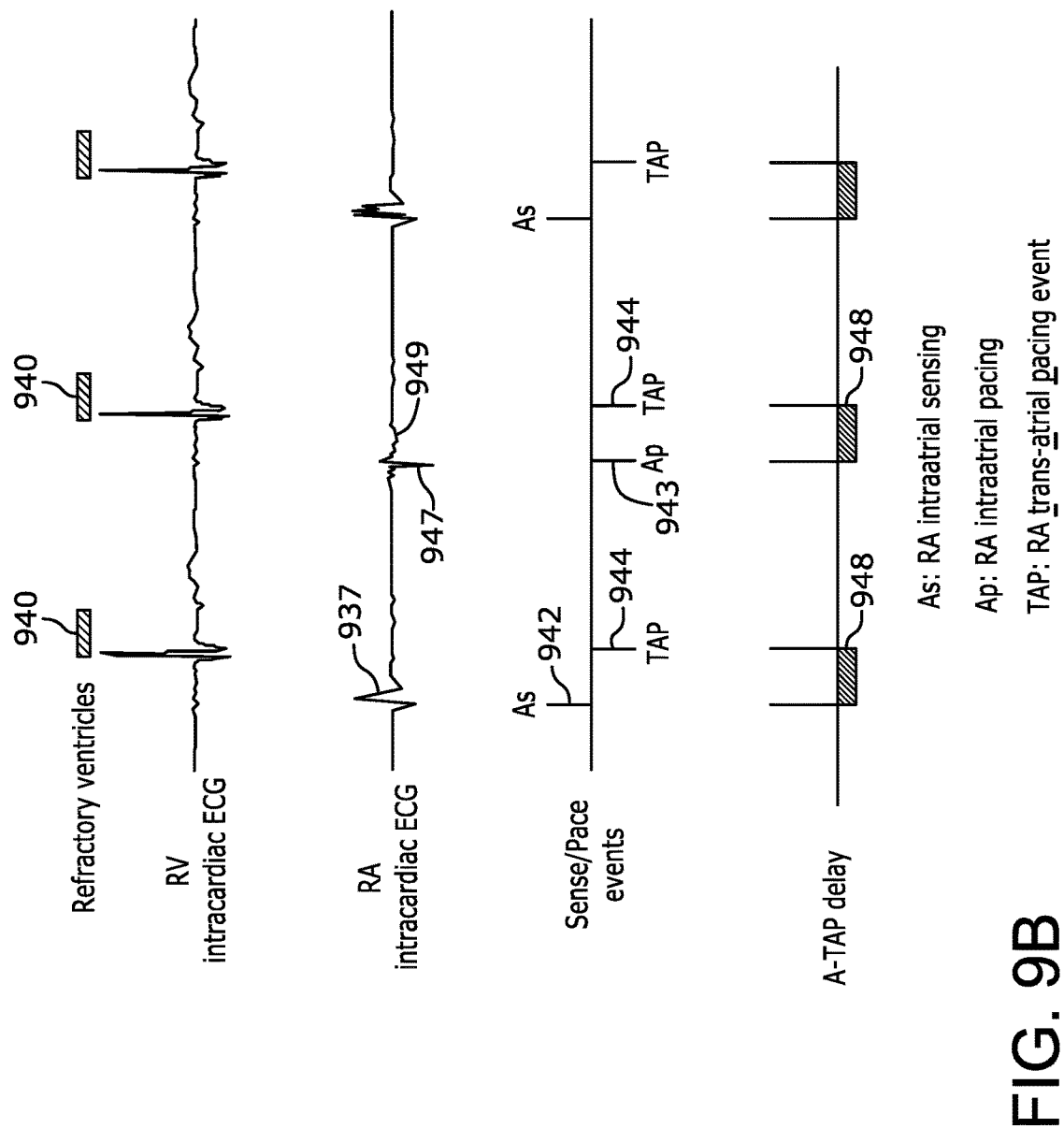
FIG. 9B is a schematic illustration of a transvenous lead implanted in the right atrium to place an ADS therapy mechanism at an interface of the right atrial wall and the diaphragm and a CRM therapy mechanism adjacent the right atrial wall, together with diagrams showing the timing relationship between sensed cardiac events, paced cardiac events, and the delivery of diaphragmatic stimulation.

FIG. 9B is a schematic illustration of a transvenous, endocardial lead 932 associated with an IMD corresponding to single chamber pacemaker operating in AAI mode and with ADS therapy capability. AAI mode corresponds to atrial demand pacing, during which the atrium is paced and sensed, and the pulse generator of the device inhibits pacing output in response to a sensed atrial event. The lead is a RA endocardial lead 932 implanted in the right atrium 934 to place an ADS therapy mechanism 900 at an interface of the right atrial wall 936 and the diaphragm 908 for purposes of delivering diaphragmatic stimulation through muscles of the diaphragm, and a CRM therapy mechanism 901 adjacent the right atrial wall for purposes of sensing atrial events and delivering atrial pacing pulses as needed. The right atrial lead 932 further includes a cardiac event sensor 903 configured to be placed in, on, or adjacent cardiac tissue to enable the sensing of electrical activity of the heart.

The various time-aligned graphs in FIG. 9B illustrate the relationship between sensed cardiac events 942, 943 and the delivery of diaphragmatic stimulation pulses 944 as enabled by the pacemaker. In this embodiment, the IMB senses valid RA events 942, 943 through the cardiac event sensor 903. A sensed RA event 942 may correspond to an intrinsic atrial event, e.g., an P wave 937 of an electrocardiogram resulting from an intrinsic, naturally conducting atrial depolarization. A sensed right atrial event 943 may correspond to an atrial pacing spike 947 of an electrocardiogram resulting from the delivery of an atrial pacing stimulus through the CRM therapy mechanism 901, or an evoked atrial depolarization 949 of an electrocardiogram, which depolarization results from and follows the delivery of an atrial pacing pulse.

Upon sensing a RA event 942, 943 the IMD delivers a diaphragmatic stimulation pulse 944, through the ADS therapy mechanism 900, at the end of a delay period 948. The delay period 948 is calculated to place delivery of the diaphragmatic stimulation pulse 944 in the refractory period 940 of the ventricle. As such, the diaphragmatic stimulation pulse 944 does not induce an evoked response, e.g. depolarization, in the heart, and only induces a transient contraction of the diaphragm.

Figure 9C:
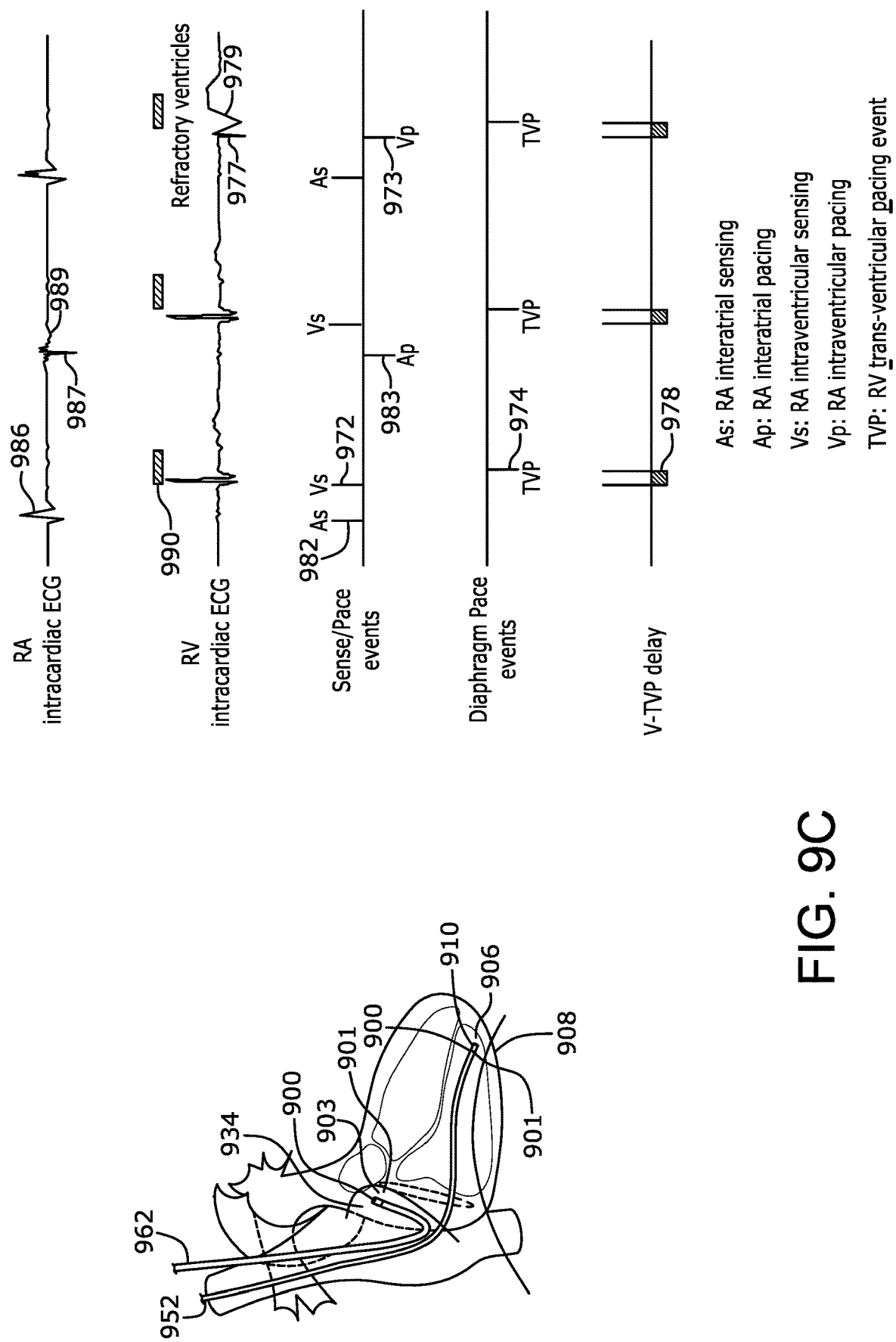
FIG. 9C is a schematic illustration of a transvenous lead implanted in the right ventricle to place an ADS therapy mechanism and a CRM therapy mechanism at an interface of the right ventricular wall and the diaphragm and a transvenous lead implanted in the right atrium to place a CRM therapy mechanism adjacent an atrial wall, together with diagrams showing the timing relationship between sensed cardiac events, paced cardiac events, and the delivery of diaphragmatic stimulation.

FIG. 9C is a schematic illustration of a pair of transvenous, endocardial leads 952, 962 associated with an IMD corresponding to a dual chamber pacemaker operating in DDD mode and with ADS therapy capability. DDD mode corresponds to dual chamber pacing, during which both the ventricle and atrium may be paced and sensed, and the pulse generator of the device inhibits ventricular pacing output in response to a sensed ventricular event, and atrial pacing output in response to a sensed atrial event. One of the leads is a RV endocardial lead 952 implanted in the right ventricle 904 to place an ADS therapy mechanism 900 at an interface of the right ventricular wall 906 and the diaphragm 908 for purposes of delivering diaphragmatic stimulation through muscles of the diaphragm, and a CRM therapy mechanism 901 adjacent the right ventricular wall for purposes of sensing ventricular events and delivering ventricular pacing pulses as needed.

The other lead is a RA endocardial lead 962 implanted in the right atrium 934 to place a CRM therapy mechanism 901 adjacent the right atrial wall for purposes of sensing atrial events and delivering atrial pacing pulses as needed. The RA endocardial lead 962 may also place an ADS therapy mechanism 900 at an interface of the right atrial wall 936 and the phrenic nerve (not shown) for purposes of delivering diaphragmatic stimulation through stimulation of the phrenic nerve, as an alternate to delivering diaphragmatic stimulation through the muscles of the diaphragm by the ADS therapy mechanism 100 of the RV endocardial lead 952. Each of these leads 952, 962 further includes a cardiac event sensor 903 configured to be placed in, on, or adjacent cardiac tissue to enable the sensing of electrical activity of the heart.

The various time-aligned graphs in FIG. 9C illustrate the relationship between sensed cardiac events 972, 973 and the delivery of diaphragmatic stimulation pulses 974 as enabled by the pacemaker. In this embodiment, the IMD senses valid RV events 972, 973 through the cardiac event sensor 903 of the RV endocardial lead 952. A sensed RV event 972 may correspond to an intrinsic ventricular event, e.g., an R wave 916 or a Q wave of an electrocardiogram resulting from an intrinsic, naturally conducting ventricular depolarization. A sensed right ventricular event 973 may correspond to a ventricular pacing spike 977 of an electrocardiogram resulting from the delivery of a ventricular pacing stimulus through the CRM therapy mechanism 901, or an evoked ventricular depolarization 979 of an electrocardiogram, which depolarization results from and follows the delivery of a ventricular pacing pulse. The IMB also senses RA events 982, 983 through the cardiac event sensor 903 of the RA endocardial lead 962. A sensed RA vent 982 may correspond to an intrinsic atrial event, e.g., an P wave 986 of an electrocardiogram resulting from an intrinsic, naturally conducting atrial depolarization. A sensed RA event 983 may correspond to an atrial pacing spike 987 of an electrocardiogram resulting from the delivery of an atrial pacing stimulus through the CRM therapy mechanism 901, or an evoked atrial depolarization 989 of an electrocardiogram, which depolarization results from and follows the delivery of an atrial pacing pulse.

Upon sensing a RV event 972, 973 the IMD delivers a diaphragmatic stimulation pulse 974, through the ADS therapy mechanism 900, at the end of a delay period 978. The delay period 978 is calculated to place delivery of the diaphragmatic stimulation pulse 974 in the refractory period 990 of the ventricle. As such, the diaphragmatic stimulation pulse 974 does not induce an evoked response, e.g. depolarization, in the heart, and only induces a transient contraction of the diaphragm.

Figure 10:
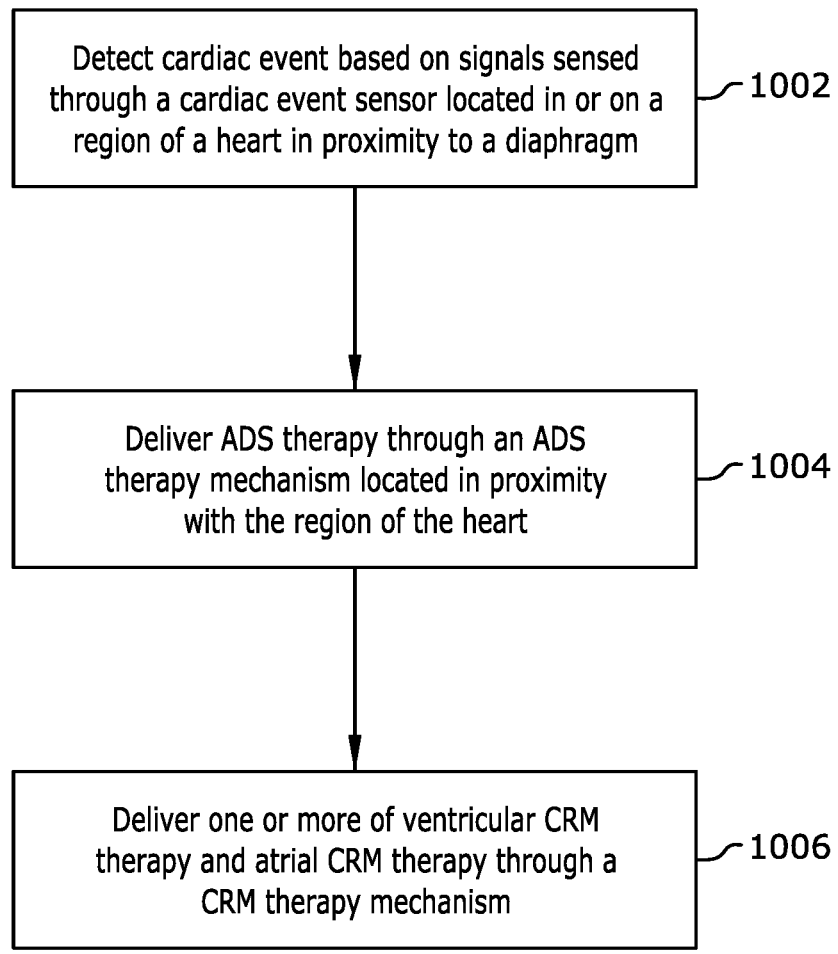
FIG. 10 is a flowchart of a method of transcardiac asymptomatic diaphragmatic stimulation that may be implemented with anyone of the implantable medical devices of FIGS. 3A, 3B, 4, 6A, and 6B.

With reference to FIG. 10, a method of transcardiac diaphragmatic stimulation may be performed by any of the embodiments of IMDs disclosed herein.

At block 1002, a cardiac event is detected by the IMD 300, 600 based on signals sensed through a cardiac event sensor 103 located in or on a region of a heart 104 in proximity to a diaphragm 106. Depending on the embodiment of the IMB 300, 600 performing the method, the region of the heart where the cardiac event sensor 103 is located may be an interface between a ventricle of the heart 104 and the diaphragm 106, or it may be an interface between an atrium of the heart 104 and the diaphragm, separated by the pericardium. Furthermore, the cardiac events sensed by the cardiac event sensor 103 may vary depending on the embodiment of the IMD 300, 600. In any case, the cardiac event may correspond to one of: an intrinsic ventricular event, a ventricular pacing spike, an evoked ventricular event, an intrinsic atrial event, an atrial pacing spike, an evoked atrial event, and a mechanical event.

At block 1004, an ADS therapy is delivered by the IMB 300, 600 through an ADS therapy mechanism 100 located in proximity with the region of the heart 104. The ADS therapy is configured to induce a contraction of the diaphragm 106 by capturing a muscle of the diaphragm or capturing a phrenic nerve 124. In some embodiments, the contraction of the diaphragm 106 induced by the ADS therapy is one or more of asymptomatic, transient, and partial. The ADS therapy is timed for delivery such that the ADS therapy does not induce a contraction of the heart 104. To this end, delivery of the ADS therapy comprises outputting a diaphragmatic stimulation pulse to the ADS therapy mechanism 100 during a refractory period of the heart 104 associated with the cardiac event. For example, as described above with reference to FIGS. 8 and 9A-9C, the diaphragmatic stimulation pulse 814, 914, 944, 974 may be output at an end of a delay period timed from an occurrence of the cardiac event that places the timing of ADS therapy within a refractory period 820, 920, 940, 990.

With reference to FIGS. 3A and 3B, the method of transcardiac diaphragmatic stimulation of FIG. 10 may be enabled by an implanted IMB 300 having an endocardial lead 304a, 306, 308 associated with a chamber of the heart.

In some embodiments, an endocardial lead 304a having a cardiac event sensor 103 and an ADS therapy mechanism 100 may be implanted in a right ventricle to enable the sensing of cardiac events corresponding to right ventricular events, and the delivery of ADS therapy timed to such events. Alternatively, an endocardial lead 308 having a cardiac event sensor 103 and an ADS therapy mechanism 100 may be implanted in a coronary sinus to enable the sensing of cardiac events corresponding to left ventricular events, and the delivery of ADS therapy timed to such events.

In addition to delivering ADS therapy, an implanted IMB 300 with a, endocardial lead 304a, 308 may also have a CRM therapy mechanism 101 for delivering a CRM therapy. Accordingly, with reference to FIG. 10, in block 1006, a CRM therapy may be delivered to induce an affect, e.g., a ventricular depolarization, in the heart. To this end, a CRM therapy in the form of cardiac pacing pulses sufficient to capture a right ventricle or a left ventricle, is output by a CRM controller 705 of the IMD to the CRM therapy mechanism 101 in accordance with a ventricular pacing therapy. The CRM therapy mechanism 101 may be located in proximity with the region of the heart where the cardiac event sensor 103 and the ADS therapy mechanism 100 are located. The CRM therapy is delivered outside the refractory period of the heart to ensure capture of the heart.

In some embodiments, an endocardial lead 306 having a cardiac event sensor 103 and an ADS therapy mechanism 100 may be implanted in a right atrium to enable sensing of cardiac events corresponding to atrial events, and the delivery of ADS therapy timed to such events.

In addition to delivering ADS therapy, an implanted IMB 300 with an endocardial lead 306 may also have a CRM therapy mechanism 101 for delivering a CRM therapy. Accordingly, with reference to FIG. 10, in block 1006, a CRM therapy may be delivered to induce an affect, e.g., an atrial depolarization, in the heart. To this end, a CRM therapy in the form of cardiac pacing pulses sufficient to capture a right atrium or a left atrium, is output by a CRM controller 705 of the IMB to the CRM therapy mechanism 101 in accordance with an atrial pacing therapy. The CRM therapy mechanism 101 may be located in proximity with the region of the heart where the cardiac event sensor 103 and the ADS therapy mechanism 100 are located. The CRM therapy is delivered outside the refractory period of the heart to ensure capture of the heart.

With continued reference to FIGS. 3A and 3B, the method of transcardiac diaphragmatic stimulation of FIG. 10 may be enabled by an implanted IMD 300 having a transcardiac lead 304b associated with a chamber of the heart and with an abdominal cavity.

In some embodiments, a transcardiac lead 304b having a cardiac event sensor 103 and an ADS therapy mechanism 100 may be implanted in one of a right atrium and a right ventricle, and partially through a cardiac wall and through the diaphragm and into the abdominal cavity. The transcardiac lead 304b is implanted to place the cardiac event sensor 103 in the heart and the ADS therapy mechanism 100 in the abdominal cavity adjacent a surface of the diaphragm, to thereby enable sensing of cardiac events corresponding to atrial events or ventricular events, and the delivery of ADS therapy timed to such events.

In addition to delivering ADS therapy, an implanted IMD 300 with a transcardiac lead 304b may also have a CRM therapy mechanism 101 for delivering a CRM therapy. Accordingly, with reference to FIG. 10, in block 1006, a CRM therapy may be delivered to induce an affect, e.g., an atrial depolarization or a ventricular depolarization, in the heart. To this end, a CRM therapy in the form of cardiac pacing pulses sufficient to capture a right atrium or a right ventricle, is output by a CRM controller 705 of the IMD to the CRM therapy mechanism 101 in accordance with an atrial or ventricular pacing therapy. The CRM therapy mechanism 101 may be located in proximity with the region of the heart where the cardiac event sensor 103 and the ADS therapy mechanism 100 are located. The CRM therapy is delivered outside the refractory period of the heart to ensure capture of the heart.

With reference to FIGS. 6A and 6B, the method of transcardiac diaphragmatic stimulation of FIG. 10 may be enabled by an implanted leadless IMD 600 having a cardiac event sensor 103 and an ADS therapy mechanism 100.

The leadless IMD 600 may be implanted between one of: 1) an atrial wall and the diaphragm, and 2) a ventricular wall and the diaphragm. The leadless IMD 600 is implanted to place the cardiac event sensor 103 adjacent a cardiac wall of the heart 104 and the ADS therapy mechanism 100 adjacent the diaphragm 106, to thereby enable sensing of cardiac events corresponding to atrial events or ventricular events, and the delivery of ADS therapy timed to such events.

In addition to delivering ADS therapy, a leadless IMD 600 may also have a CRM therapy mechanism 101 for delivering CRM therapy. Accordingly, with reference to FIG. 10, in block 1006, a CRM therapy may be delivered to induce an affect, e.g., an atrial depolarization or a ventricular depolarization, in the heart. To this end, a CRM therapy in the form of cardiac pacing pulses sufficient to capture a right atrium or a right ventricle, is output by a CRM controller 705 of the IMD to the CRM therapy mechanism 101 in accordance with an atrial or ventricular pacing therapy. The CRM therapy is delivered outside the refractory period of the heart to ensure capture of the heart.

Thus disclosed herein is transcardiac diaphragmatic stimulation that includes detecting a cardiac event based on signals sensed through a cardiac event sensor located in or on a region of a heart in proximity to a diaphragm, and delivering an ADS therapy through an ADS therapy mechanism that is located in proximity with the region of the heart, to induce a contraction of the diaphragm without inducing a contraction of the heart. The cardiac event sensor may be located a) on an interior surface of a cardiac wall that abuts the diaphragm, or 2) on an exterior surface of a heart, between a cardiac wall and the diaphragm. The ADS therapy mechanism may be located: a) on an interior surface of a cardiac wall that abuts the diaphragm, 2) on a superior surface of the diaphragm that abuts a cardiac wall, or 3) on an inferior surface of the diaphragm at a region of the diaphragm that abuts the heart.

Also disclosed herein is a method of ADS therapy through a CRM device that is capable of sensing cardiac activity from endocardial/epicardial sensing leads and delivering cardiac stimulation pulses in support of an indicated pacing therapy, e.g., anti-bradycardia/cardiac resynchronization therapy. To this end, an endocardial and/or transcardiac pacing/sensing lead(s) is placed in either the right atrium and/or right ventricle and/or or left ventricle (coronary sinus lead, epicardial lead) in support of the indicated pacing therapy. An ADS therapy mechanism is placed to allow for close proximity to the diaphragm and/or phrenic nerve. In some embodiments, a pacing lead of the CRM device is designated the ADS therapy mechanism and delivers ADS therapy. The pacing lead may be either the endocardial/epicardial lead used by the CRM device to deliver the indicated pacing therapy, or a transcardiac lead with a design tailored to support both the delivery of the pacing therapy and the ADS therapy. The designated lead may be one of a right ventricular lead, a right atrial lead, a left chamber (coronary sinus) lead, or a transcardiac lead.

The method also includes sensing the electrical (or mechanical) activity of the heart chamber associated with the designated lead, registering when that heart chamber is contracting and its cells are depolarized and refractory to further electrical stimulation. Such registering may be either through evidence in a sensed electrical signal, e.g., register an intra/extracardiac electrogram and detect a P or R wave, or through the initiation of a pacing pulse delivered in the heart chamber as part of an indicated pacing therapy. The method further includes, upon detection of a cardiac event corresponding to chamber contraction, starting a delay timer (programmed or calculated value to ensure that the heart's atria and ventricle are refractory when it timed out and the ADS pulse delivery is effective), and delivering an energy pulse at the end of the calculated/programmed delay sufficient to capture the diaphragmatic muscle and evoke a transient, partial contraction of the diaphragm in support of an ADS therapy.

The various aspects of this disclosure are provided to enable one of ordinary skill in the art to practice the present invention. Various modifications to exemplary embodiments presented throughout this disclosure will be readily apparent to those skilled in the art, and the concepts disclosed herein may be extended to other magnetic storage devices. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A method of transcardiac diaphragmatic stimulation, the method comprising:
   detecting a cardiac event based on signals sensed through a cardiac event sensor located in or on a region of a heart in proximity to a diaphragm; and
   responsive to a detection of a cardiac event, delivering an asymptomatic diaphragmatic stimulation (ADS) therapy through an ADS therapy mechanism located in proximity with the region of the heart, to capture a muscle of the diaphragm to induce a transient contraction of a portion of a hemisphere of the diaphragm that is less than the entirety of the hemisphere of the diaphragm, without inducing a contraction of the heart.

2. The method of claim 1, wherein the region of the heart is at an interface between one of:
   a ventricle of the heart and the diaphragm, or
   an atrium of the heart and the diaphragm, separated by a pericardium.

3. The method of claim 1, further comprising confirming the transient contraction of the diaphragm.

4. The method of claim 1, wherein delivering an ADS therapy comprises outputting a diaphragmatic stimulation pulse to the ADS therapy mechanism during a refractory period of the heart associated with the cardiac event.

5. The method of claim 4, wherein the diaphragmatic stimulation pulse is output at an end of a delay period timed from an occurrence of the cardiac event.

6. The method of claim 1, wherein the cardiac event corresponds to one of: an intrinsic ventricular event, a ventricular pacing spike, an evoked ventricular event, an intrinsic atrial event, an atrial pacing spike, an evoked atrial event, and a mechanical event.

7. The method of claim 1, wherein the cardiac event sensor and the ADS therapy mechanism are each included in a lead associated with a chamber of the heart.

8. The method of claim 7, wherein the lead is implanted in one of a right ventricle and a coronary sinus, and the cardiac event corresponds to a ventricular event.

9. The method of claim 8, further comprising delivering a cardiac rhythm management (CRM) therapy through a CRM therapy mechanism to induce an affect in the heart, wherein the CRM therapy is delivered outside a refractory period of the heart.

10. The method of claim 9, wherein delivering a CRM therapy comprises:
outputting cardiac pacing pulses to the CRM therapy mechanism in accordance with a ventricular pacing therapy, the cardiac pacing pulses corresponding to the CRM therapy and being sufficient to capture a right ventricle or a left ventricle.

11. The method of claim 7, wherein the lead is implanted in one of a right atrium and a coronary sinus, and the cardiac event corresponds to an atrial event.

12. The method of claim 11, further comprising delivering a cardiac rhythm management (CRM) therapy through a CRM therapy mechanism to induce an affect in the heart, wherein the CRM therapy is delivered outside a refractory period of the heart.

13. The method of claim 12, wherein delivering a CRM therapy comprises:
outputting cardiac pacing pulses to the CRM therapy mechanism in accordance with an atrial pacing therapy, the cardiac pacing pulses corresponding to the CRM therapy and being sufficient to capture a right atrium or a left atrium.

14. The method of claim 1, wherein:
the cardiac event sensor and the ADS therapy mechanism are each included in a leadless device that is implanted between one of: 1) an atrial wall and the diaphragm, and 2) a ventricular wall and the diaphragm.

15. The method of claim 14, further comprising delivering a cardiac rhythm management (CRM) therapy through a CRM therapy mechanism to induce an affect in the heart, wherein the CRM therapy is delivered outside a refractory period of the heart.

16. The method of claim 15, wherein delivering a CRM therapy comprises:
outputting cardiac pacing pulses to the CRM therapy mechanism in accordance with a pacing therapy, the cardiac pacing pulses corresponding to the CRM therapy and being sufficient to capture a right ventricle or a right atrium.

17. The method of claim 1, wherein the transient contraction lasts in the range of 60 milliseconds (msec) to 180 msec.

18. An implantable medical device comprising:
a cardiac event sensor configured to be located in or on a region of a heart in proximity to a diaphragm;
an asymptomatic diaphragmatic stimulation (ADS) therapy mechanism configured to be located in proximity with the region of the heart; and
an ADS controller coupled to the cardiac event sensor and the ADS therapy mechanism, and configured to:
detect a cardiac event based on signals sensed through the cardiac event sensor; and
responsive to a detection of a cardiac event, deliver an ADS therapy to the diaphragm through the ADS therapy mechanism,
wherein the ADS therapy is configured to capture a muscle of the diaphragm to induce a transient contraction of a portion of a hemisphere of the diaphragm that is less than the entirety of the hemisphere of the diaphragm, and is delivered during a refractory period of the heart associated with the cardiac event to avoid inducing a contraction of the heart.

19. The implantable medical device of claim 18, wherein the ADS controller is configured to output a diaphragmatic stimulation pulse to the ADS therapy mechanism at an end of delay period timed from an occurrence of the cardiac event.

20. The implantable medical device of claim 18, wherein:
the cardiac event sensor comprises either a first pair of electrodes or a motion sensor,
the ADS therapy mechanism comprises either a second pair of electrodes or a mechanical transducer, and
the ADS therapy comprises either electrical stimulation or mechanical stimulation.

21. The implantable medical device of claim 20, wherein the first pair of electrodes and the second pair of electrodes are a same pair of electrodes.

22. The implantable medical device of claim 20, wherein the first pair of electrodes and the second pair of electrodes are different pairs of electrodes.

23. The implantable medical device of claim 20, wherein the mechanical transducer is configured to provide signals corresponding to motion of the diaphragm.

24. The implantable medical device of claim 20, wherein the ADS therapy mechanism further comprises a motion sensor configured to provide signals corresponding to motion of the diaphragm.

25. The implantable medical device of claim 18, further comprising a lead that includes the cardiac event sensor and the ADS therapy mechanism, wherein the lead is configured to be associated with a chamber of the heart.

26. The implantable medical device of claim 25, wherein the lead comprises an endocardial lead configured to be implanted in one of a right ventricle, a right atrium, and a coronary sinus.

27. The implantable medical device of claim 25, wherein the lead comprises an epicardial lead configured to be implanted in a pericardial space and over one of a right ventricle, a right atrium, a left ventricle.

28. The implantable medical device of claim 25, wherein the lead comprises a transcardiac lead configured to be implanted in a right ventricle and at least partially through a cardiac wall and into a diaphragm.

29. The implantable medical device of claim 28, wherein the transcardiac lead comprises:
a lead body having a distal end and a proximal end;
a distal end structure associated with the distal end and having a distal portion configured to extend through a cardiac wall into a diaphragm, and to transition from an undeployed state during which the distal portion has a first cross-section diameter to a deployed state during which the distal portion has a second cross-section diameter greater than the first cross-section diameter; and
at least one electrode associated with the distal portion.

30. The implantable medical device of claim 18, further comprising a leadless device that includes the cardiac event sensor, the ADS therapy mechanism, and the ADS controller, the leadless device configured to be implanted between one of:
an atrial wall and the diaphragm, and
a ventricular wall and the diaphragm.

31. The implantable medical device of claim 30, wherein:
the leadless device comprises a housing having a first side and a second side opposite the first side;
the cardiac event sensor is associated with the first side; and
the ADS therapy mechanism is associated with on the second side.

32. The implantable medical device of claim 18, wherein the ADS therapy mechanism comprises one or more of: at least one electrode configured to deliver electrical stimulation, and a mechanical transducer configured to deliver mechanical stimulation.

33. The implantable medical device of claim 18, wherein the ADS therapy mechanism further comprises a motion sensor configured to provide signals representing motion of the diaphragm, and wherein the ADS controller is further configured to monitor motion of the diaphragm based on signals from the motion sensor to confirm the contraction of the diaphragm.

34. The implantable medical device of claim 18, further comprising:
a cardiac rhythm management (CRM) therapy mechanism configured to be located in or on a region of the heart; and
a CRM controller coupled to the CRM therapy mechanism and configured to output cardiac pacing pulses to the CRM therapy mechanism in accordance with a pacing therapy, the cardiac pacing pulses corresponding to the CRM therapy and being sufficient to capture the heart.

35. The implantable medical device of claim 34, wherein the CRM therapy mechanism corresponds to one of the cardiac event sensor or the ADS therapy mechanism.

36. The implantable medical device of claim 34, wherein the CRM therapy mechanism comprises a pair of electrodes independent of the cardiac event sensor and the ADS therapy mechanism.

37. The implantable medical device of claim 18, wherein the transient contraction lasts in the range of 60 milliseconds (msec) to 180 msec.

38. A method of transcardiac diaphragmatic stimulation, the method comprising:
detecting a cardiac event based on signals sensed through a cardiac event sensor located in or on a region of a heart in proximity to a diaphragm; and
delivering an asymptomatic diaphragmatic stimulation (ADS) therapy through an ADS therapy mechanism located in proximity with the region of the heart, to induce a contraction of the diaphragm without inducing a contraction of the heart,
wherein the cardiac event sensor and the ADS therapy mechanism are each included in a lead implanted in one of a right atrium and a right ventricle, and having a distal end structure with a portion that extends through a cardiac wall, and through the diaphragm, and into an abdominal cavity.

39. The method of claim 38, wherein the ADS therapy mechanism is associated with the portion that extends through a cardiac wall, and through the diaphragm, and into the abdominal cavity, and is located in or on a region of the diaphragm in proximity to the heart.

40. The method of claim 38, further comprising delivering a cardiac rhythm management (CRM) therapy through a CRM therapy mechanism, outside a refractory period of the heart to induce an affect in the heart.

41. The method of claim 40, wherein delivering a CRM therapy comprises:
outputting cardiac pacing pulses to the CRM therapy mechanism in accordance with a pacing therapy, the cardiac pacing pulses corresponding to the CRM therapy and being sufficient to capture a right ventricle or the right atrium.

42. An implantable medical device comprising:
a cardiac event sensor configured to be located in or on a region of a heart in proximity to a diaphragm;
an asymptomatic diaphragmatic stimulation (ADS) therapy mechanism configured to be located in proximity with the region of the heart; and
an ADS controller coupled to the cardiac event sensor and the ADS therapy mechanism, and configured to:
detect a cardiac event based on signals sensed through the cardiac event sensor; and
deliver an ADS therapy to the diaphragm through the ADS therapy mechanism,
wherein the cardiac event sensor and the ADS therapy mechanism are each included in a lead configured to be implanted in one of a right atrium and a right ventricle, wherein the lead comprises a distal end structure with a portion configured to extend through a cardiac wall, and through the diaphragm, and into an abdominal cavity.

* * * * *